(12) United States Patent
Haake et al.

(10) Patent No.: US 6,699,482 B2
(45) Date of Patent: Mar. 2, 2004

(54) LEPTOSPIRA RARE OUTER MEMBRANE PROTEINS

(75) Inventors: David A. Haake, Culver City, CA (US); Ellen S. Shang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/992,807

(22) Filed: Nov. 13, 2001

(65) Prior Publication Data

US 2002/0127240 A1 Sep. 12, 2002

Related U.S. Application Data

(60) Continuation of application No. 09/193,441, filed on Nov. 17, 1998, now abandoned, which is a division of application No. 08/444,646, filed on May 19, 1995, now Pat. No. 5,837,263.

(51) Int. Cl.[7] .................. A61K 39/02; C12P 21/02; C07K 1/00
(52) U.S. Cl. .................. 424/234.1; 424/190.1; 435/69.1; 435/69.3; 435/71.1; 530/300; 530/350; 536/23.7
(58) Field of Search .................. 424/190.1, 234.1; 435/69.1, 69.3, 71.1; 530/300, 350; 536/23.7

(56) References Cited

U.S. PATENT DOCUMENTS

| | | |
|---|---|---|
| 4,366,246 A | 12/1982 | Riggs |
| 4,474,893 A | 10/1984 | Reading |
| 4,676,980 A | 6/1987 | Segal et al. |
| 4,916,567 A | 4/1990 | Grobecker et al. |
| 5,091,301 A | 2/1992 | Zuerner |

OTHER PUBLICATIONS

Hookey,J.V., et al "The use of 16s rDNA sequence analysis to investigate the phylogeny of Leptospiraceae and related spirochaetes", Journal of General Microbiology, vol. 139, pp. 2585–2590, 1993.*
Haake, et al., "Characterization of Leptospiral Outer Membrane Lipoprotein LipL36: Downregulation Associated with Late–Log–Phase Growth and Mammalian Infection," *Infection and Immunity*, 66(4):1579–1587 (1998).
Shang, et al., "Molecular Cloning and Sequence Analysis of the Gene Encoding LipL41, a Surface–Exposed Lipoprotein of Pathogenic Leptospira Species" *Infection and Immunity*, 64(6):2322–2330 (1996).
Shang, et al., "Molecular Cloning and Sequence Analysis of the Genes Encoding Two Leptospiral Lipoproteins, LipL1 and LipL2," Abstracts of the General Meeting of the American Society for Microbiology (1995) 95(0):249. Abstract D–2. Meeting Info.: 95th General Meeting of the American Society for Microbiology Washington, D.C., USA May 21–25 (995).

Akins, D. R., et al., "Lipid Modification of the 17–Kilodalton Membrane Immunogen of *Treponema pallidum* Determines Macrophage Activation as well as Amphiphilicity", *Infect. Immun.*, 61:1202 (1993).
Baril, C., et al., "Sizing of the Leptospira genome by pulsed–field agarose gel electrophoresis", *FEMS Microbiology Letters*, 71:95 (1990).
Bolin, C. A., et al., "Effect of vaccination with a pentavalent leptospiral vaccine on *Leptospira interrogans* serovar hardjo type hardjo–bovis infection of pregnant cattle", *Am. J. Vet. Res.*, 50:161 (1989).
Bolin, C. A., et al., "Effect of vaccination with a pentavalent leptospiral vaccine containing *Leptospira interrogans* serovar hardjo type hardjo–bovis on type hardjo–bovis infection of cattle", *Am. J. Vet. Res.*, 50:2004 (1989).
Bolin, C. A., "Effect of vaccination with a monovalent *Leptospira interrogans* serovar hardjo type hardjo–bovis vaccine on type hardjo–bovin infection of cattle", et al., *Am. J. Vet. Res.*, 52:1639 (1993).
Brandt, et al., "Immunogenic Integral Membrane Proteins of *Borrelia burgdorferi* Are Lipoproteins", *Infect. Immun.*, 58:983 (1990).
Chamberlain, N. R., et al., "Major Integral Membrane Protein Immunogens of *Treponema pallidum* Are Proteolipids", *Infect. Immun.*, 57:2872 (1989).
Chamberlain, N. R., et al., "Acylation of the 47–Kilodalton Major Membrane Immunogen of *Treponema pallidum* Determines Its Hydrophobicity", *Infect. Immun.*, 57:2878 (1989).
Cunningham, et al., "Selective Release of the *Treponema pallidum* Outer Membrane and Associated Polypeptides with Triton X–114", *J. Bacteriol.*, 170:5789 (1988).
DNA Related of Leptospiraceae Serovars (Prepublication Listing Subject to Revision), Emerging Bacterial and Mycotic Diseases Branch, Division of Bacterial and Myocotic Diseases, National Center for Infections Diseases, Centers for Disease Control and Prevention, Atlanta, GA 30333 (Jun. 7, 1994).
Doherty, J. P., et al., Biology Abstract, *Immunology*, 87(11):AB–477, Ref. No. 115457.
Farr, R. W., "Leptospirosis", State–Of–The–Art Clinical Article, *Clinical Infections Diseases*, 21:1 (1995).

(List continued on next page.)

*Primary Examiner*—Rodney P Swartz
(74) *Attorney, Agent, or Firm*—Gray Cary Ware & Freidenrich, LLP; Lisa A. Haile; Richard J. Imbra

(57) ABSTRACT

The present invention presents novel leptospiral membrane lipoproteins, LipL1 and LipL2, associated with pathogenic strains of Leptospira. LipL1 is of about 35 kDa, and LipL2 is of about 41 kDa. Also disclosed are the method for purifying these proteins from Leptospira, their nucleotide and amino acid sequences, the cloning of the genes encoding the proteins and their recombinant proteins, methods for producing antibodies to these proteins, the resulting antibodies. These proteins, their immunogenic fragments, and antibodies against them, are useful for inducing an immune response to pathogenic Leptospira as well as providing a diagnostic target for leptospirosis.

10 Claims, 13 Drawing Sheets

OTHER PUBLICATIONS

Haake, D. A., et al., "Changes in the surface of *Leptospira interrogans* Serovat grippotyphosa during In Vitro Cultivation", *Infection & Immunity,* 59:1131 (1991).

Haake, D. A., et al., "Molecular Cloning and Sequence Analysis of the Gene Encoding OmpL1, a Transmembrane Outer Membrane Protein of Pathogenic Leptospira spp.", *J. Bacteriol.,* 175:4225 (1993).

Hayashi, S., et al., "Lipoproteins in Bacteria", *J. Bioenerg. Biomembr.,* 22:451 (1990).

Miyamoto, M., et al., "Molecular Cloning and Sequence Analysis of Antigen Gene tdpA if *Treponema denticola"*, *Infect. Immun.,* 59:1941 (1991).

Penn, C. W., et al., "Genetic approaches to cell biology and metabolism of spirochetes", *Res. Microbiol.,* 143:605 (1992).

Ramadass, P., et al., "Genetic Characterization of Pathogenic Leptospira Species by DNA Hybridization", *Int'l. J. of Systematic Bacteriol.,* 42:215 (1992).

Richaud, C., et al., "Cloning of genes required for amino acid biosynthesis from *leptospira interrogans* serovar icterohaemorrhagiae", *J. of Gen. Microbiology,* 136:651 (1990).

Sambrook, J., et al., Molecular Cloning: A Laboratory Manual, 2nd ed., Cold Spring Harbor Laboratory, Cold Spring Harbor, NY (1989).

Stamm, et al., "Changes in the Cell Surface Properties of *Treponema pallidum* That Occur during In Vitro Incubation of Freshly Extracted Organisms", *Infect. Immun.,* 55:2255 (1987).

Thiermann, et al., "Leptospirosis: Current developments and trends", *J. Am. Vet. Med. Assoc.,* 184:722 (1984).

Thiermann, A. B., et al., "Improved Techniques for the Isolation of Leptospires from Swine Abortion Cases", *Ann. Proc. Amer. Assn. Veterinary Laboratory Diagnosticians,* 27:233 (1984).

Thomas, W., et al., "Molecular Cloning, Expression, and DNA Sequence Analysis of the Gene That Enclodes the 16–Kilodalton Outer Membrane Lipoprotein of *Serpulina hyodysenteriae"*, *Infect. Immun.,* 61:1136 (1993).

Van Eys, G. J. J. M., et al., "DNA Hybridization with Hardjobovis–specific Recombinant Probes as a Method for Type Discrimination of *Leptospira interrogans* Serovar hardjo", *J. of Gen. Microbiology,* 134:567 (1988).

von Heijne, G., "The structure of signal peptides from bacterial lipoproteins", *Protein Engineering,* 2:531 (1989).

Yang, N.–S., et al., "Gene Transfer via Particle Bombardment: Applications of the Accell Gene Gun", *Gene Therapeutics: Methods and Applications of Direct Gene Transfer,* Wolff, J. A. ed., Brikhauser, p. 193, USA (1994).

Yasuda, P. H., et al., "Deoxyribonucleic Acid Relatedness between Serogroups and Serovars in the Family of Leptospiraceae with Proposals for Seven New LeiptospiraSpecies", *Int'l. J. Systematic Bacteriology,* 37:407 (1987).

Zuerner, et al., "Characterization of outer membrane and secreted proteins of *Leptospira interrogans* serovar pomona", *Microbial. Pathogenesis,* 10:311 (1991).

Cinco, M., et al., "Immunodominant antigens recognized by the human immune response to infection by organisms of the species *Leptospira Interrogans* serogroup Australis", FEMS Microbiology Letters, 89: 287 (1992).

Brown et al., "Protein and Antigen Profiles of Prevalent Serovars of *Leptospira interrogans*", Infection and Immunity, vol. 59, No. 5, pp. 1772–1777, especially figure 2, issued May 1991.

Gitton et al., "Immunoblotting Study of the antigenic relationships among eight serogroups of Leptospira", Veterinary microbiology, vol. 32, pp. 293–303, especially Figures 1–3, issued 1992.

Knudsen, "Proteins Transferred to Nitrocellulose for Use as Immunogens", Analytical Biochemistry, vol. 147, pp. 285–288, issued 1985.

* cited by examiner

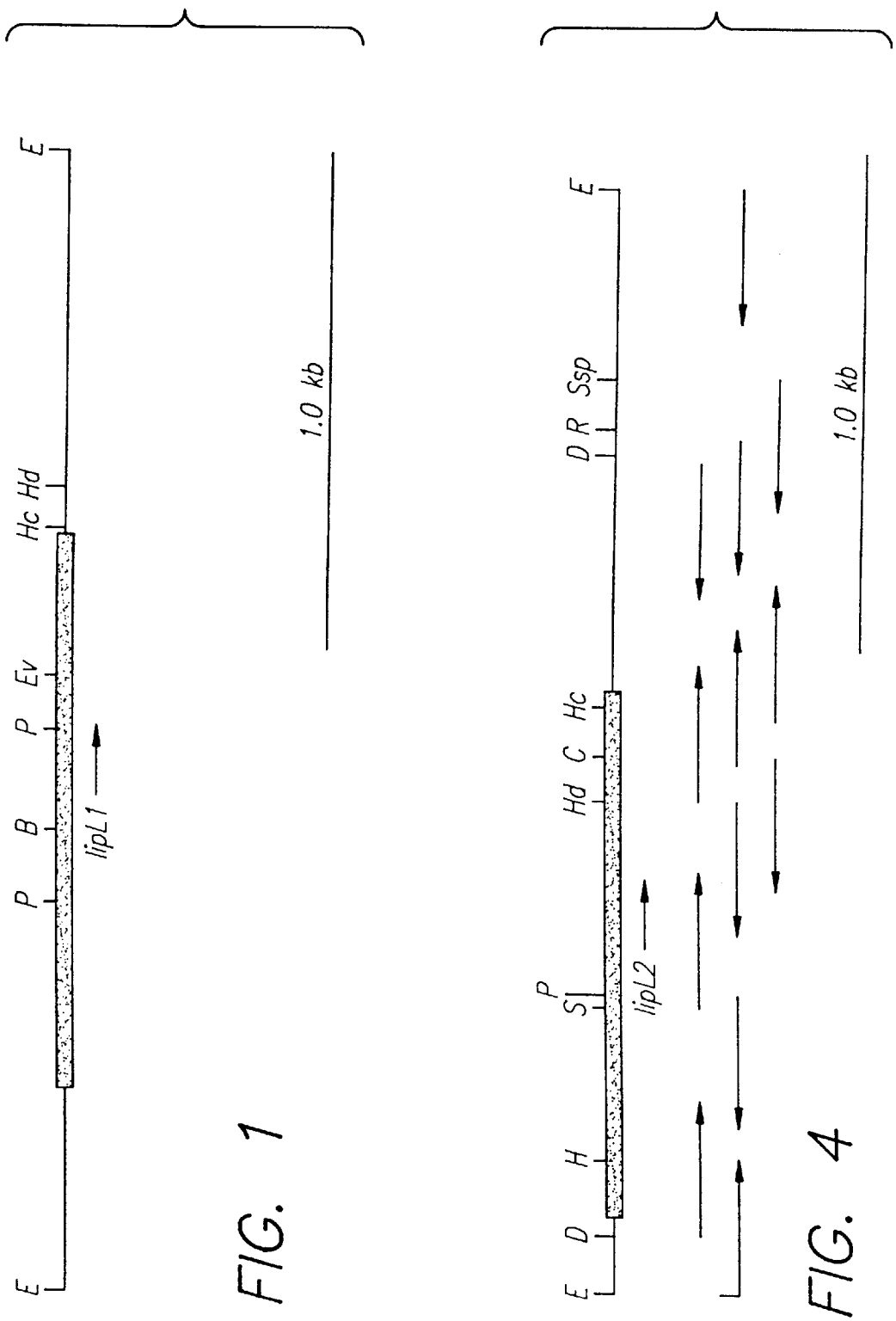

FIG. 2

```
  1 AGATATAGATATTTTTTATAAAAACTATGGCCTAAAAAGATTCACTTTTCTGTATAGTATTTGACCTAATTTCTACAC
                                                                    ---
                                                                    -35

80 TTAAGGAATATTATAGACCAGAAGTGATTCCATAATCACTTAAAAATCACAAGAGGTTCTTTCTTT ATG AGA AGA
       ---                                        RBS                 Met Arg Arg
       -10
```

| | | | | | | | | | | | | | | | | | | | |
|---|---|---|---|---|---|---|---|---|---|---|---|---|---|---|---|---|---|---|---|
|156|AAC|ATA|ATG|AAA|ATT|GCC|GCT|GTA|GCA|GCT|CTT|ACG|GTT|GCT|TTA|ACG|GCA|TGT|AAA|AGT|
| |Asn|Ile|Met|Lys|Ile|Ala|Ala|Val|Ala|Ala|Leu|Thr|Val|Ala|Leu|Thr|Ala|Cys|Lys|Ser|
|216|GAC|GAC|GAT|GAT|GAC|GAT|GTT|ATG|TTG|GCG|CTT|TTG|TAT|TTA|GCA|GAT|CAA|ACA|AGC|
| |Asp|Asp|Asp|Asp|Asp|Asp|Val|Met|Leu|Ala|Leu|Leu|Tyr|Leu|Ala|Asp|Gln|Thr|Ser|
|276|GGA|AAT|TGC|GTG|ACA|CTA|AAG|GAT|GAC|GCT|GCG|CAT|AAT|GGT|GCA|GGA|GCA|GGG|
| |Gly|Asn|Cys|Val|Thr|Leu|Lys|Asp|Asp|Ala|Ala|His|Asn|Gly|Ala|Gly|Ala|Gly|
|336|GAT|GGA|AAA|CCT|ACT|TAT|ACA|GCA|ACT|GGT|AAT|ACA|AGA|CCA|AAA|GCA|GCC|TGT|GCA|GGT|
| |Asp|Gly|Lys|Pro|Thr|Tyr|Thr|Ala|Thr|Gly|Asn|Thr|Arg|Pro|Lys|Ala|Ala|Cys|Ala|Gly|
|396|ACT|TTT|AAC|ACA|GTT|TTT|ATT|GTA|AAC|GAT|GCA|GAG|GCG|GTA|GCG|ACT|TCG|GTT|AAA|GCC|
| |Thr|Phe|Asn|Thr|Val|Phe|Ile|Val|Asn|Asp|Ala|Glu|Ala|Val|Ala|Thr|Ser|Val|Lys|Ala|
|456|GCC|TAT|CAG|GCA|GCT|AAG|GAT|GCA|GTG|GCA|TCT|GGC|TCA|AAT|TGT|GCA|GCT|GTA|AGC|
| |Ala|Tyr|Gln|Ala|Ala|Lys|Asp|Ala|Val|Ala|Ser|Gly|Ser|Asn|Cys|Ala|Ala|Val|Ser|
|516|ACA|GCT|CTT|CAA|GCG|GCA|ACA|GAC|CTT|GTA|ACA|TCG|CTT|AAA|GTA|CAG|CAA|ACA|CTT|GCA|
| |Thr|Ala|Leu|Gln|Ala|Ala|Thr|Asp|Leu|Val|Thr|Ser|Leu|Lys|Val|Gln|Gln|Thr|Leu|Ala|

FIG. 2A

576 AGC ACT GGC TTC TGT GCA AAT CTA GGC ACA GAT TGG AAC CTT AAC CTA TTA ACT TTT GGT
    Ser Thr Gly Phe Cys Ala Asn Leu Gly Thr Asp Trp Asn Leu Asn Leu Leu Thr Phe Gly

636 GGA AGT TCA GTG AGT GTG GAT CCT AAT TCT GAG TAT TTT GGA AAG ACT GTA TTG GTA TGT
    Gly Ser Ser Val Ser Val Asp Pro Asn Ser Glu Tyr Phe Gly Lys Thr Val Leu Val Cys

696 CCT TCC GAA CAG CCA AAG CAG AAA CAA ATC GTC TTA TTG AGT AGT CTA AAC TTT TCA ACG
    Pro Ser Glu Gln Pro Lys Gln Lys Gln Ile Val Leu Leu Ser Ser Leu Asn Phe Ser Thr

756 ATT GCT GGG TCA GTA GCA ACC GAT ATG ACA ACT AAC CTT GCT TTT AGA CAA AAA AGT GCT
    Ile Ala Gly Ser Val Ala Thr Asp Met Thr Thr Asn Leu Ala Phe Arg Gln Lys Ser Ala

816 GCA GTT ACT GCA TCC AAT TTT AAA TGG ACT GCG GAT GCA GCT GCT AAA GGT CGT TTA ATC
    Ala Val Thr Ala Ser Asn Phe Lys Trp Thr Ala Asp Ala Ala Ala Lys Gly Arg Leu Ile

876 AAT GTT ACT GAA CTA ACA ACT GCA GGT AAA TCA GGA GCG GCT TTA GTT GCT TTT AGA TCG
    Asn Val Thr Glu Leu Thr Thr Ala Gly Lys Ser Gly Ala Ala Leu Val Ala Phe Arg Ser

936 GCA GTT TTG GCT GCT GGT GCT ACT TGT GCA AAA GAT ATC TTA TCC AAG GAA AGT GAA GAG
    Ala Val Leu Ala Ala Gly Ala Thr Cys Ala Lys Asp Ile Leu Ser Lys Glu Ser Glu Glu

996 GCA CAG CGC ATT GCT TTC TCT CTA CAT GAT CAA GGT CAA GCT GGT TTT AAT GGT GCG ACA
    Ala Gln Arg Ile Ala Phe Ser Leu His Asp Gln Gly Gln Ala Gly Phe Asn Gly Ala Thr

1056 GGT GTA GTT TTA GAC TCT ATA ATT ACT ACT GCT CAA GCA CAG TCT GCA ACA GAA GTT CTT
     Gly Val Val Leu Asp Ser Ile Ile Thr Thr Ala Gln Ala Gln Ser Ala Thr Glu Val Leu

FIG. 2B

```
1116 TTT ACT AGC CTT ACT TGT AAA TAT GGT GAT TTT GAT GAA GAA AAT ACG GGT AAC AAG ACT
     Phe Thr Ser Leu Thr Cys Lys Tyr Gly Asp Phe Asp Glu Glu Asn Thr Gly Asn Lys Thr

1176 ACA GTT GGA ACT GAG ACA AAC GTA AAA AAT ACC GGA ACT TGT CCT GCA ACT TAT CCT AGA
     Thr Val Gly Thr Glu Thr Asn Val Lys Asn Thr Gly Thr Cys Pro Ala Thr Tyr Pro Arg

1236 TAC TAATTCTTTTTAGAATTAAGTTAACGGAAAAATACCGCACTACTTTTAGTGCGGTATTTTTTTGAGA
     Tyr *

1314 AAAGATATTCCTGAGAACCTCTCTAATTCTGAAAAAGCTTTTTTGAATTAAATTCTTGAATCATTTCAATTTTTAT

1393 CATGTTTTATATAAAGTCGCCTTTAAGTGATTTCAGTGGGTGAGTTTTGTTCACTCATTTTAGATAGTGAACAAAATG

1472 ATAAAACGTTATTTTTTAAGAAATATGAATCATCATATTTAATTCTCTAATGTATGTAGATTACTCCGGCGATTTTGC
```

FIG. 5

1   CTTGTATGAGAAGTGTCTCTTCAATCAAAAAAAGAAGAACAAAGATCCATTTTCAAATCCTAATTTTCGATTCTA

80  AAATCATTGACATGATTCTTTTGGATTTTAAATCATCCCTTATTCCCAAAATCAAACAGGATTGGTGTTACTTTTC
          -35                        -10                              RBS

159 ATG AGA AAA TTA TCT TCT CTA ATT TCT GTG TTA GTT CTC CTT ATG TTC TTA GGA AAT TGC
    Met Arg Lys Leu Ser Ser Leu Ile Ser Val Leu Val Leu Leu Met Phe Leu Gly Asn Cys

219 GCA GCT ACA GTT GAT GTA GAA TAT CCG GTA TTC CCG AAA GAT AAA GAA GGC CGT GCA CTT
    Ala Ala Thr Val Asp Val Glu Tyr Pro Val Phe Pro Lys Asp Lys Glu Gly Arg Ala Leu

279 CAA AAA TTC CTC GGA ACC ATT CGT AAC GTA GGT TTG GCT GTA GAA GCT CCT AAA AAA AGT
    Gln Lys Phe Leu Gly Thr Ile Arg Asn Val Gly Leu Ala Val Glu Ala Pro Lys Lys Ser

339 CTT TGG GAA GCG ATC TTC GGT GAA GGT TCC AGT TTT ATT GAT CAG ATG CCT TCT AAA GTT
    Leu Trp Glu Ala Ile Phe Gly Glu Gly Ser Ser Phe Ile Asp Gln Met Pro Ser Lys Val

399 TTC GAG GCG TTT GAC AAA GAG TCT TAT TAC AAA CTT ACC GAC TTG AGC AAA CGT GCA GAC
    Phe Glu Ala Phe Asp Lys Glu Ser Tyr Tyr Lys Leu Thr Asp Leu Ser Lys Arg Ala Asp

459 GCA ATC AAC GAA GCG AGT CTT TCT CTT ACA GGA ATT ACT AAA AAC AGA GCA AAG ATC GGA
    Ala Ile Asn Glu Ala Ser Leu Ser Leu Thr Gly Ile Thr Lys Asn Arg Ala Lys Ile Gly

FIG. 5A

```
519 AAT CTG ATC GGA GAA GCA ATT CTA TAC ATA GGT TAT CAA AAA CCT TAT ACA GAG TGT
    Asn Leu Ile Gly Glu Ala Ile Leu Tyr Ile Gly Tyr Gln Lys Pro Tyr Thr Glu Cys

579 AGT ACT GAA AAT AAA GTC GAT GCG GTT GCA GCT GGT TTG AAA GTG GCT GGT TTT GCC GCT
    Ser Thr Glu Asn Lys Val Asp Ala Val Ala Ala Gly Leu Lys Val Ala Gly Phe Ala Ala

639 TCT ATG GCA ACT GGT AAA GAC GTA AAT ACA GGA AAC GAA CCA GTA TCT AAA CCT ACT GGA
    Ser Met Ala Thr Gly Lys Asp Val Asn Thr Gly Asn Glu Pro Val Ser Lys Pro Thr Gly

699 GTG CGT ATG ATG TTA ATT CCT CTC GAT GCT ACT CTC ATC AAA GTA GAA ACC GGA GAA GTA
    Val Arg Met Met Leu Ile Pro Leu Asp Ala Thr Leu Ile Lys Val Glu Thr Gly Glu Val

759 AAA AAG GCG GTA GTT TCC AGT CCT GCG AAA ATT TAC AAC AGT GTA GGA AAT TTA GAA TGC
    Lys Lys Ala Val Val Ser Ser Pro Ala Lys Ile Tyr Asn Ser Val Gly Asn Leu Glu Cys

819 CCT TCA ATT TTA GAT TCT TTC GGA CAA GGT TTG GAT GAA GCT GCT GCT ATA TYR ATC AAG GGC
    Pro Ser Ile Leu Asp Ser Phe Gly Gln Gly Leu Asp Glu Ala Ala Ala Tyr Ile Lys Gly

879 AGA CTT TCT CCA ATT GTT AAA ACA GAA AGA ATT AAA GTT TTT GTT AAA GAC GAA GAC GAA
    Arg Leu Ser Pro Ile Val Lys Thr Glu Arg Ile Lys Val Phe Val Lys Asp Glu Asp Glu

939 GAA GTA AAA GAA CTT CTT CAA GAA GGT TAC GAA GAA ATC GTT GGT GAA ACT CCA AGT TTC
    Glu Val Lys Glu Leu Leu Gln Glu Gly Tyr Glu Glu Ile Val Gly Glu Thr Pro Ser Phe
```

FIG. 5B

```
999  AAA AAA GCA AAA GAA AAA GCT TGG GAA AAA GCT GAT AAA AAA GCA AAA GGT CAG TCT TGG GGA
     Lys Lys Ala Lys Glu Lys Ala Trp Glu Lys Ala Asp Lys Lys Ala Lys Gly Gln Ser Trp Gly

1059 GCA AAA GCA AAC CTT GCA ACC TAC TAT TTT TCA GCA GGT GAT TTT GAA AAA TCG ATT AAA
     Ala Lys Ala Asn Leu Ala Thr Tyr Tyr Phe Ser Ala Gly Asp Phe Glu Lys Ser Ile Lys

1119 CTC TAC GAA GAA GCT ATG AAA TTG AAA GAT GCT GAT AAG AGC TAT CTG AGA GAA CTT AGA
     Leu Tyr Glu Glu Ala Met Lys Leu Lys Asp Ala Asp Lys Ser Tyr Leu Arg Glu Leu Arg

1179 AAA AGA GTA GAG GCT ACT TTC GCC GTT GAC GAA AGC AAC GCA AAG TAATCGGGTTCCTTTGAAA
     Lys Arg Val Glu Ala Thr Phe Ala Val Asp Glu Ser Asn Ala Lys *
                                                                           <·········

1243 TTACAAAATTGTATGAAAAGCGGGCGAAAAGTCCGCTTTTCTTATTTTATCCTAATCTTCTCAACTTTATTTCTTATC
                          ·········>

1322 GAGTGTAGAAAAACTCCGAACGAAGAAGAATGTGTAGAAAAATCAAATGCACAACGTACTTTCCCCGTTCCGAAAACCA

1401 ACCCCAAAGTAATCGGGTTCCCTTTGAAATTACCCAAATTGTTGAAAAGCGGGCGAAAAGGCCCCCTTTTCTTATTT

1480 TTATCCTAATCTTCTCAACTTTATTTCTTATCGAGTGTAGAAAAACTCCGCCCGAAGAAGAATGTGTAGAAAATCAAAT
```

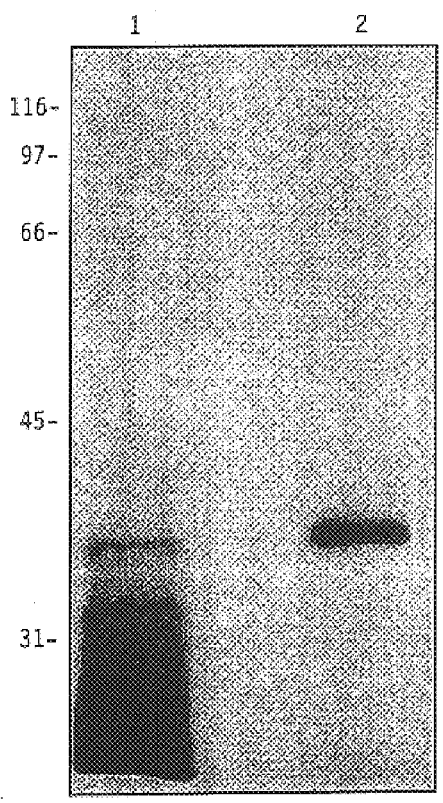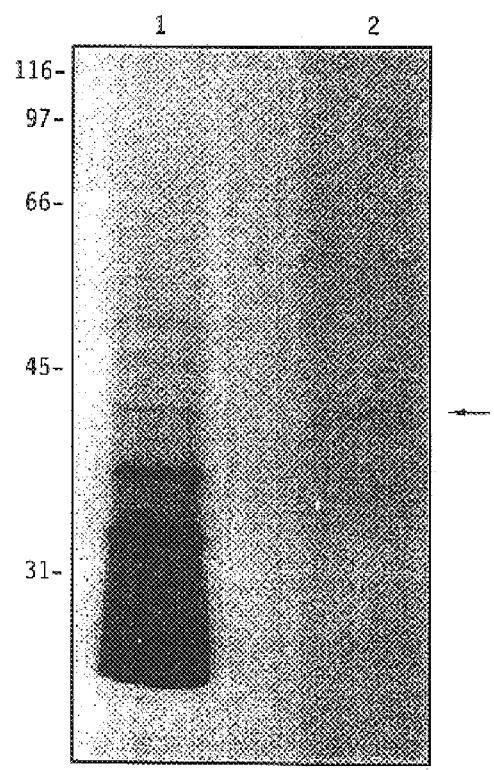
FIG. 7
FIG. 8

SEQUENCE LISTING

<160> NUMBER OF SEQ ID NOS: 14

<210> SEQ ID NO 1
<211> LENGTH: 1550
<212> TYPE: DNA
<213> ORGANISM: Leptospira kirschneri

<400> SEQUENCE: 1

```
agatatagat atttttttat aaaaactatg gcctaaaaag attcactttt ctgtatagta      60
tttgacctaa tttctacact taaggaatat tatagaccag aaagtgattc cataatcact     120
taaaaatcac aagaggttct ttctttatga gaagaaacat aatgaaaatt gccgctgtag     180
cagctcttac ggttgcttta acggcatgta aaagtgacga cgatgatgac gatgttgtta     240
tgttggcgct tttgtattta gcagatcaaa caagcggaaa ttgcgtgaca ctaacaaagg     300
atgacgctgc gcataatggt gctgcaggag caggggatgg aaaacctact tatacagcaa     360
ctggtaatac aagaccaaaa gcagcctgtg caggtacttt taacacagtt tttattgtaa     420
acgatgcaga ggcggtagcg acttcggtta aagccgccta tcaggcagct aaggataagg     480
cagtggcatc tggctcaaat tgtgcagctg taagcacagc tcttcaagcg gcaacagacc     540
ttgtaacatc gcttaaagta cagcaaacac ttgcaagcac tggcttctgt gcaaatctag     600
gcacagattg gaaccttaac ctattaactt ttggtggaag ttcagtgagt gtggatccta     660
attctgagta ttttggaaag actgtattgg tatgtccttc cgaacagcca aagcagaaac     720
aaatcgtctt attgagtagt ctaaacttt caacgattgc tgggtcagta gcaaccgata     780
tgacaactaa ccttgctttt agacaaaaaa gtgctgcagt tactgcatcc aattttaaat     840
ggactgcgga tgcagctgct aaaggtcgtt taatcaatgt tactgaacta acaactgcag     900
gtaaatcagg agcggcttta gttgcttta gatcggcagc tttggctggt gctgctactt     960
gtgcaaaaga tatcttatcc aaggaaagtg aagaggcaca gcgcattgct ttctctctac    1020
atgatcaagg tgctggtttt aatggtgcgg taacaggtgt agttttagac tctataatta    1080
ctactgctca agcacagtct gcaacagaag ttctttttac tagccttact tgtaaatatg    1140
gtgattttga tgaagaaaat acgggtaaca agactacagt tggaactgag acaaacgtaa    1200
aaaataccgg aacttgtcct gcaacttatc ctagatacta attcttttta gaatttaatt    1260
taagttaacg gaaaaatacc gcactacttt ttagtgcggt atttttttg agaaaagata    1320 ttcctgagaa cctctctaat tctgaaaaag ctttttttga atttaaattc ttgaatcatt    1380
ttcaattttt atcatgtttt atataaagtc gcctttaagt gatttcagtg ggtgagtttt    1440
gttcactcat ttttagatag tgaacaaaat gataaaacgt tattttttaa gaaatatgaa    1500
```

-continued

```
tcatcatatt ttaattctct aatgtatgta gattactccg gcgattttgc            1550

<210> SEQ ID NO 2
<211> LENGTH: 1092
<212> TYPE: DNA
<213> ORGANISM: Leptospira kirschneri

<400> SEQUENCE: 2
atgagaagaa acataatgaa aattgccgct gtagcagctc ttacggttgc tttaacggca      60
tgtaaaagtg acgacgatga tgacgatgtt gttatgttgg cgcttttgta tttagcagat     120
caaacaagcg gaaattgcgt gacactaaca aaggatgacg ctgcgcataa tggtgctgca     180
ggagcagggg atggaaaacc tacttataca gcaactggta atacaagacc aaaagcagcc     240
tgtgcaggta cttttaacac agtttttatt gtaaacgatg cagaggcggt agcgacttcg     300
gttaaagccg cctatcaggc agctaaggat aaggcagtgg catctggctc aaattgtgca     360
gctgtaagca cagctcttca agcggcaaca gaccttgtaa catcgcttaa agtacagcaa     420
acacttgcaa gcactggctt ctgtgcaaat ctaggcacag attggaacct taacctatta     480
acttttggtg gaagttcagt gagtgtggat cctaattctg agtattttgg aaagactgta     540
ttggtatgtc cttccgaaca gccaaagcag aaacaaatcg tcttattgag tagtctaaac     600
ttttcaacga ttgctgggtc agtagcaacc gatatgacaa ctaaccttgc ttttagacaa     660
aaaagtgctg cagttactgc atccaatttt aaatggactg cggatgcagc tgctaaaggt     720
cgtttaatca atgttactga actaacaact gcaggtaaat caggagcggc tttagttgct     780
tttagatcgg cagctttggc tggtgctgct acttgtgcaa aagatatctt atccaaggaa     840
agtgaagagg cacagcgcat tgctttctct ctacatgatc aaggtgctgg ttttaatggt     900
gcggtaacag gtgtagtttt agactctata attactactg ctcaagcaca gtctgcaaca     960
gaagttcttt ttactagcct tacttgtaaa tatggtgatt ttgatgaaga aaatacgggt    1020
aacaagacta cagttggaac tgagacaaac gtaaaaaata ccggaacttg tcctgcaact    1080
tatcctagat ac                                                        1092

<210> SEQ ID NO 3
<211> LENGTH: 364
<212> TYPE: PRT
<213> ORGANISM: Leptospira kirschneri

<400> SEQUENCE: 3

Met Arg Arg Asn Ile Met Lys Ile Ala Ala Val Ala Ala Leu Thr Val
1               5                   10                  15

Ala Leu Thr Ala Cys Lys Ser Asp Asp Asp Asp Asp Asp Val Val Met
            20                  25                  30

Leu Ala Leu Leu Tyr Leu Ala Asp Gln Thr Ser Gly Asn Cys Val Thr
        35                  40                  45

Leu Thr Lys Asp Asp Ala Ala His Asn Gly Ala Ala Gly Ala Gly Asp
    50                  55                  60

Gly Lys Pro Thr Tyr Thr Ala Thr Gly Asn Thr Arg Pro Lys Ala Ala
65                  70                  75                  80

Cys Ala Gly Thr Phe Asn Thr Val Phe Ile Val Asn Asp Ala Glu Ala
                85                  90                  95

Val Ala Thr Ser Val Lys Ala Ala Tyr Gln Ala Ala Lys Asp Lys Ala
            100                 105                 110

Val Ala Ser Gly Ser Asn Cys Ala Ala Val Ser Thr Ala Leu Gln Ala
```

|  | 115 |  |  | 120 |  |  |  | 125 |  |  |  |
|---|---|---|---|---|---|---|---|---|---|---|---|

Ala Thr Asp Leu Val Thr Ser Leu Lys Val Gln Gln Thr Leu Ala Ser
130                 135                 140

Thr Gly Phe Cys Ala Asn Leu Gly Thr Asp Trp Asn Leu Asn Leu Leu
145                 150                 155                 160

Thr Phe Gly Gly Ser Ser Val Ser Val Asp Pro Asn Ser Glu Tyr Phe
            165                 170                 175

Gly Lys Thr Val Leu Val Cys Pro Ser Glu Gln Pro Lys Gln Lys Gln
            180                 185                 190

Ile Val Leu Leu Ser Ser Leu Asn Phe Ser Thr Ile Ala Gly Ser Val
            195                 200                 205

Ala Thr Asp Met Thr Thr Asn Leu Ala Phe Arg Gln Lys Ser Ala Ala
210                 215                 220

Val Thr Ala Ser Asn Phe Lys Trp Thr Ala Asp Ala Ala Lys Gly
225                 230                 235                 240

Arg Leu Ile Asn Val Thr Glu Leu Thr Ala Gly Lys Ser Gly Ala
            245                 250                 255

Ala Leu Val Ala Phe Arg Ser Ala Ala Leu Ala Gly Ala Ala Thr Cys
            260                 265                 270

Ala Lys Asp Ile Leu Ser Lys Glu Ser Glu Glu Ala Gln Arg Ile Ala
            275                 280                 285

Phe Ser Leu His Asp Gln Gly Ala Gly Phe Asn Gly Ala Val Thr Gly
290                 295                 300

Val Val Leu Asp Ser Ile Ile Thr Thr Ala Gly Ala Gln Ser Ala Thr
305                 310                 315                 320

Glu Val Leu Phe Thr Ser Leu Thr Cys Lys Tyr Gly Asp Phe Asp Glu
            325                 330                 335

Glu Asn Thr Gly Asn Lys Thr Thr Val Gly Thr Glu Thr Asn Val Lys
            340                 345                 350

Asn Thr Gly Thr Cys Pro Ala Thr Tyr Pro Arg Tyr
            355                 360

<210> SEQ ID NO 4
<211> LENGTH: 1558
<212> TYPE: DNA
<213> ORGANISM: Leptospira kirschneri

<400> SEQUENCE: 4

```
cttgtatgag aagtgtctct tcaatcaaaa aaagaaagaa caaagatcc atttttcaaa      60 tcctaattttt tcgattctaa atcattgac atgattcttt ttggatttttt aaatcatccc     120 ttattcccca aaatcaaaca ggattggtgt tactttttcat gagaaaatta tcttctctaa    180
tttctgtgtt agttctcctt atgttcttag gaaattgcgc agctacagtt gatgtagaat     240
atccggtatt cccgaaagat aaagaaggcc gtgcacttca aaaattcctc ggaaccattc     300
gtaacgtagg tttggctgta gaagctccta aaaaagtct ttgggaagcg atcttcggtg      360
aaggttccag ttttattgat cagatgcctt ctaaagtttt cgaggcgttt gacaaagagt     420
cttattacaa acttaccgac ttgagcaaac gtgcagacgc aatcaacgaa gcgagtcttt     480
ctcttacagg aattactaaa aacagagcaa agatcggaaa tctgatcgga gcagaagcaa    540
ttctatacat aggttatcaa aaaccttata cagagtgtag tactgaaaat aaagtcgatg     600
cggttgcagc tggtttgaaa gtggctggtt ttgccgcttc tatggcaact ggtaaagacg    660
taaatacagg aaacgaacca gtatctaaac ctactggagt gcgtatgatg ttaattcctc    720
```

-continued

```
tcgatgctac tctcatcaaa gtagaaaccg gagaagtaaa aaaggcggta gtttccagtc      780
ctgcgaaaat ttacaacagt gtaggaaatt tagaatgccc ttcaattta gattctttcg       840 gacaaggttt ggatgaagct gctgcttata tcaagggcag actttctcca attgttaaaa     900
cagaaagaat taaagttttt gttaaagacg aagacgaaga agtaaaagaa cttcttcaag     960
aaggttacga agaaatcgtt ggtgaaactc caagtttcaa aaaagcaaaa gaagcttggg   1020
aaaaagctga taaaaaagca aaggtcagt cttggggagc aaaagcaaac cttgcaacct     1080
actatttttc agcaggtgat tttgaaaaat cgattaaact ctacgaagaa gctatgaaat   1140
tgaaagatgc tgataagagc tatctgagag aacttagaaa aagagtagag gctactttcg   1200
ccgttgacga aagcaacgca aagtaatcgg gttcctttga aattacaaaa ttgtatgaaa   1260
agcgggcgaa aagtccgctt ttcttatttt tatcctaatc ttctcaactt tatttcttat   1320
cgagtgtaga aaaactccga acgaagaaga atgtgtagaa aaatcaaatg cacaacgtac   1380
tttccccgtt ccgaaaacca accccaaagt aatcgggtt ccctttgaaa ttacccaaat    1440
tgtttgaaaa gcgggcgaaa aggccccctt ttcttatttt tatcctaatc ttctcaactt   1500
tatttcttat cgagtgtaga aaaactccgc ccgaagaaga atgtgtagaa aatcaaat     1558
```

<210> SEQ ID NO 5
<211> LENGTH: 1065
<212> TYPE: DNA
<213> ORGANISM: Leptospira kirschneri

<400> SEQUENCE: 5

```
atgagaaaat tatcttctct aatttctgtg ttagttctcc ttatgttctt aggaaattgc       60
gcagctacag ttgatgtaga atatccggta ttcccgaaag ataaagaagg ccgtgcactt     120
caaaaattcc tcggaaccat tcgtaacgta ggtttggctg tagaagctcc taaaaaaagt    180 cttgggaag cgatcttcgg tgaaggttcc agttttattg atcagatgcc ttctaaagtt      240
ttcgaggcgt ttgacaaaga gtcttattac aaacttaccg acttgagcaa acgtgcagac    300
gcaatcaaca agcgagtct ttctcttaca ggaattacta aaaacagagc aaagatcgga     360
aatctgatcg gagcagaagc aattctatac ataggttatc aaaaacctta tacagagtgt    420
agtactgaaa ataagtcga tgcggttgca gctggtttga agtggctgg ttttgccgct     480 tctatggcaa ctggtaaaga cgtaaataca ggaaacgaac cagtatctaa acctactgga    540
gtgcgtatga tgttaattcc tctcgatgct actctcatca agtagaaac cggagaagta    600 aaaaaggcgg tagtttccag tcctgcgaaa atttacaaca gtgtaggaaa tttagaatgc    660
ccttcaattt tagattcttt cggacaaggt ttggatgaag ctgctgctta tatcaagggc    720
agactttctc caattgttaa aacagaaaga attaaagttt ttgttaaaga cgaagacgaa    780
gaagtaaaag aacttcttca agaaggttac gaagaaatcg ttggtgaaac tccaagtttc    840
aaaaaagcaa agaagcttg ggaaaaagct gataaaaaag caaaggtca gtcttgggga    900 gcaaaagcaa accttgcaac ctactatttt tcagcaggtg attttgaaaa atcgattaaa   960
ctctacgaag aagctatgaa attgaaagat gctgataaga gctatctgag agaacttaga   1020
aaaagagtag aggctacttt cgccgttgac gaaagcaacg caaag                   1065
```

<210> SEQ ID NO 6
<211> LENGTH: 355
<212> TYPE: PRT
<213> ORGANISM: Leptospira kirschneri

<400> SEQUENCE: 6

```
Met Arg Lys Leu Ser Ser Leu Ile Ser Val Leu Val Leu Leu Met Phe
1               5                   10                  15

Leu Gly Asn Cys Ala Ala Thr Val Asp Val Glu Tyr Pro Val Phe Pro
            20                  25                  30

Lys Asp Lys Glu Gly Arg Ala Leu Gln Lys Phe Leu Gly Thr Ile Arg
            35                  40                  45

Asn Val Gly Leu Ala Val Glu Ala Pro Lys Lys Ser Leu Trp Glu Ala
        50                  55                  60

Ile Phe Gly Glu Gly Ser Ser Phe Ile Asp Gln Met Pro Ser Lys Val
65                  70                  75                  80

Phe Glu Ala Phe Asp Lys Glu Ser Tyr Tyr Lys Leu Thr Asp Leu Ser
                85                  90                  95

Lys Arg Ala Asp Ala Ile Asn Glu Ala Ser Leu Ser Leu Thr Gly Ile
                100                 105                 110

Thr Lys Asn Arg Ala Lys Ile Gly Asn Leu Ile Gly Ala Glu Ala Ile
            115                 120                 125

Leu Tyr Ile Gly Tyr Gln Lys Pro Tyr Thr Glu Cys Ser Thr Glu Asn
    130                 135                 140

Lys Val Asp Ala Val Ala Ala Gly Leu Lys Val Ala Gly Phe Ala Ala
145                 150                 155                 160

Ser Met Ala Thr Gly Lys Asp Val Asn Thr Gly Asn Glu Pro Val Ser
                165                 170                 175

Lys Pro Thr Gly Val Arg Met Met Leu Ile Pro Leu Asp Ala Thr Leu
                180                 185                 190

Ile Lys Val Glu Thr Gly Glu Val Lys Lys Ala Val Val Ser Ser Pro
            195                 200                 205

Ala Lys Ile Tyr Asn Ser Val Gly Asn Leu Glu Cys Pro Ser Ile Leu
        210                 215                 220

Asp Ser Phe Gly Gln Gly Leu Asp Glu Ala Ala Ala Tyr Ile Lys Gly
225                 230                 235                 240

Arg Leu Ser Pro Ile Val Lys Thr Glu Arg Ile Lys Val Phe Val Lys
                245                 250                 255

Asp Glu Asp Glu Glu Val Lys Glu Leu Leu Gln Glu Gly Tyr Glu Glu
                260                 265                 270

Ile Val Gly Glu Thr Pro Ser Phe Lys Lys Ala Lys Glu Ala Trp Glu
            275                 280                 285

Lys Ala Asp Lys Lys Ala Lys Gly Gln Ser Trp Gly Ala Lys Ala Asn
        290                 295                 300

Leu Ala Thr Tyr Tyr Phe Ser Ala Gly Asp Phe Glu Lys Ser Ile Lys
305                 310                 315                 320

Leu Tyr Glu Glu Ala Met Lys Leu Lys Asp Ala Asp Lys Ser Tyr Leu
                325                 330                 335

Arg Glu Leu Arg Lys Arg Val Glu Ala Thr Phe Ala Val Asp Glu Ser
                340                 345                 350

Asn Ala Lys
        355

<210> SEQ ID NO 7
<211> LENGTH: 22
<212> TYPE: PRT
<213> ORGANISM: Leptospira kirschneri

<400> SEQUENCE: 7

Tyr Phe Gly Lys Thr Val Leu Val Arg Pro Ser Glu Gln Ala Lys Gln
```

```
1               5               10              15
Lys Gln Ile Val Leu Leu
                20

<210> SEQ ID NO 8
<211> LENGTH: 23
<212> TYPE: DNA
<213> ORGANISM: Artificial sequence
<220> FEATURE:
<223> OTHER INFORMATION: Degenerate probe
<220> FEATURE:
<221> NAME/KEY: misc_feature
<222> LOCATION: (9)..(9)
<223> OTHER INFORMATION: n is any nucleotide

<400> SEQUENCE: 8
garcargcna arcaraarca rat                                              23

<210> SEQ ID NO 9
<211> LENGTH: 8
<212> TYPE: PRT
<213> ORGANISM: Leptospira kirschneri

<400> SEQUENCE: 9

Glu Gln Ala Lys Gln Lys Gln Ile
1               5

<210> SEQ ID NO 10
<211> LENGTH: 18
<212> TYPE: PRT
<213> ORGANISM: Leptospira kirschneri

<400> SEQUENCE: 10

Ala Ser Leu Ser Leu Thr Gly Ile Thr Lys Asn Arg Ala Lys Ile Gly
1               5                   10                  15
Asn Leu

<210> SEQ ID NO 11
<211> LENGTH: 20
<212> TYPE: DNA
<213> ORGANISM: Artificial sequence
<220> FEATURE:
<223> OTHER INFORMATION: Degenerate probe
<220> FEATURE:
<221> NAME/KEY: misc_feature
<222> LOCATION: (12)..(12)
<223> OTHER INFORMATION: n is any nucleotide

<400> SEQUENCE: 11
acdggdatha cnaaraaymg                                                  20

<210> SEQ ID NO 12
<211> LENGTH: 7
<212> TYPE: PRT
<213> ORGANISM: Leptospira kirschneri

<400> SEQUENCE: 12

Thr Gly Ile Thr Lys Asn Arg
1               5

<210> SEQ ID NO 13
<211> LENGTH: 30
<212> TYPE: DNA
<213> ORGANISM: Artificial sequence
<220> FEATURE:
<223> OTHER INFORMATION: Amplification primer
```

-continued

```
<400> SEQUENCE: 13
ttaacgagat ctaaaagtga cgacgatgat                              30

<210> SEQ ID NO 14
<211> LENGTH: 30
<212> TYPE: DNA
<213> ORGANISM: Artificial sequence
<220> FEATURE:
<223> OTHER INFORMATION: Amplification primer

<400> SEQUENCE: 14
catgataaaa attgaaaatg attcaagaat                              30
```

LEPTOSPIRA RARE OUTER MEMBRANE PROTEINS

The present application is a continuation of U.S. patent application Ser. No. 09/193,441, filed Nov. 17, 1998, now abandoned, which is a divisional of U.S. patent application Ser. No. 08/444,646, filed May 19, 1995, now issued as U.S. Pat. No. 5,837,263.

This invention was made with Government support through funding from the Veterans' Administration Medical Research Funds, an NIH Multidisciplinary Training Grant in Microbial Pathogenesis 2-T32-AI07323-06, and awards from the United States Public Health Service under Grant Numbers AI 21352, AI 29733, and AI 12601.

TECHNICAL FIELD OF THE INVENTION

This invention relates generally to an antigenic preparation and specifically to Leptospira membrane proteins which are used to induce a protective immune response in animals. Such proteins can be used immunologically as vaccines for leptospirosis caused by this organism. Alternatively, diagnosis of leptospirosis can be performed by detecting the presence of the proteins, antibodies to the proteins, or polynucleotides which encode the proteins.

BACKGROUND OF THE INVENTION

Leptospirosis is an important, global human and veterinary health problem. It is a widespread zoonotic disease caused by pathogenic strains of Leptospira which are capable of infecting most mammalian species. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospiras have the capacity for both long-term survival in the environment as well as persistent infection and shedding by wildlife and livestock. Currently available leptospiral vaccines produce short-term immunity and do not provide cross-protection against many of the 170 serovars of pathogenic Leptospira {Thiermann, et al., *J. Am. Vet. Med. Assoc.*, 184:722 (1984)}. These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide-like substance (LLS) may confer a degree of protection. Commercially available vaccines, which consist of heat or formalin-killed leptospiras, produce incomplete or only short-term immunity, requiring their administration annually or semi-annually. In the case of *L. interrogans* serovar hardjo, the common bovine pathogen in North America, vaccines prepared in this way are ineffective {Bolin, C. A., et al., *Am. J Vet. Res.,* 50:161–165 (1989) and Bolin, C. A., et al., *Am. J. Vet. Res.,* 50:2004–2008 (1989)}. Thus there is an important need for development of an improved leptospiral vaccine.

The pathogenesis of leptospirosis is very similar to that of other spirochetal diseases, including syphilis (caused by *Treponema pallidum*) and Lyme borreliosis (caused by *Borrelia burgdorferi*). Both syphilis and Lyme borreliosis are characterized by widespread dissemination early in the course of disease, including invasion of the central nervous system. Leptospira share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis.

Lipid-modified, integral membrane proteins have been identified in a broad range of bacterial species {Hayashi, S., et al., *J. Bioenerg. Biomembr.,* 22:451–471 (1990)}. In gram-negative bacteria, these lipoproteins are processed by signal peptidase II {Pugsley, A. P., *Microbiol. Rev.,* 57:50–108 (1993)} after covalent linkage of three fatty acid residues to an N-terminal cysteine {Hantke, et al., *Eur. J. Biochem.,* 34:384–296 (1973)}. The fatty acid residues anchor the lipoproteins to either the cytoplasmic membrane or the outer membrane. Although the polypeptide portion of lipoproteins is generally hydrophilic, lipid modification renders them amphiphilic and causes them to partition into the hydrophobic phase during Triton X-114 phase partitioning {Chamberlain, N. R., et al., *Infect. Immun.,* 57:2872–2877 (1989)}.

Lipoproteins have been identified in a number of spirochetes including, *Treponema pallidum* {Chamberlain, N. R., et al., *Infect. Immun.,* 57:2872–2877 (1989) and Chamberlain, N. R., et al., *Infect. Immun.,* 57:2878–2885 (1989)}, *Treponema denticola* {Miyamoto, M., et al., *Infect. Immun.,* 59:1941–1947 (1991)}, *Serpulina hyodysenteriae* {Thomas, W., et al., *Infect. Immun.,* 61:1136–1140 (1993)}, *Borrelia burgdorferi* {Brandt, et al., *Infect. Immun.,* 58:983–991 (1990)}, and the relapsing-fever Borreliae {Burman, N., et al., *Mol. Microbiol.,* 4:1715–1726 (1990)}. The lipoproteins appear to play an important role in the pathogenesis of spirochetal diseases. For example, many of the *T. pallidum* lipoproteins are immunodominant antigens, eliciting a strong humoral and cellular immune response {Akins, D. R., et al., *Infect. Immun.,* 61:1202–1210 (1993)}. In addition, Outer Surface Protein A (OspA), of *Borrelia burgdorferi* is immunoprotective in animal models of Lyme disease {Fikrig, E., et al., *Science,* 250:553–556 (1990)}.

Triton X-114 solubilized material from both virulent and attenuated *L. kirschneri* (formerly *L. alstoni* and *L. interrogans*) strains partitioned into the hydrophobic detergent phase, and contained lipopolysaccharide like substance (LLS) from the organisms' outer membrane components {Haake, D. A., et al., *Infection & Immunity,* 59:1131–40 (1991)}. In the study, the virulent strain of *L. kirschneri* contained greater amounts of an LLS component with an apparent molecular mass of 30 kilodalton (kDa). A later Haake, D. A., et al. publication discloses the cloning and sequencing of a gene encoding the OmpL1 (with a predicted molecular weight of 31,113 Da) protein of pathogenic Leptospira spp {Haake, D. A., et al., *J. Bacteriol.,* 175:4225–4234 (1993)}. This might be the first spirochetal transmembrane outer membrane protein for which the structural gene has been cloned and sequenced.

Unsuccessful research on the identification of Leptospira and *T. pallidum* OMPs has shown the importance of taking into account spirochetal outer membrane fragility and the lack of outer membrane selectivity of ionic detergents such as sodium dodecyl sulfate (SDS) {Cunningham, et al., *J. Bacteriol.,* 170:5789 (1988); Penn, et al., *J. Gen. Microbiol.,* 131:2349 (1985); Stamm, et al., *Infect. Immun.,* 55:2255 (1987)}. Outer membrane proteins are of great importance because they play a key role in bacterial pathogenesis. The identification of outer membrane proteins involved in Leptospira pathogenesis is significant to understanding not only leptospiral outer membrane proteins and their involvement in pathogenesis, but also to understanding other spirochetal outer membrane proteins and their role in pathogenesis.

SUMMARY OF THE INVENTION

The present invention presents two novel leptospiral membrane proteins: LipL1 and LipL2. In particular, these proteins are lipoproteins which are associated with pathogenic strains of Leptospira. LipL1 is about 35 kDa, and LipL2 is about 41 kDa. Also disclosed are the method for purifying these proteins from Leptospira, their nucleotide and amino acid sequences, the cloning of the genes encoding the proteins and their recombinant proteins, methods for producing antibodies to these proteins, and the resulting antibodies. These proteins, their immunogenic fragments, and antibodies capable of binding to them, are useful for inducing an immune response to pathogenic Leptospira as well as providing a diagnostic target for leptospirosis.

BRIEF DESCRIPTION OF THE DRAWINGS

FIG. 1 presents the partial restriction map of the 2.3-kb EcoRI fragment containing the lipL1 gene and strategy for determining the nucleotide sequence. The lipL1 gene is 1092 base pairs in length. The arrow below the map indicate the direction and extent of sequence analysis. Single letters above the map indicate the following restriction enzymes: EcoRI (E), PvuII (P), Bam HI (B), EcoRV (Ev), Hinc II (Hc), and Hind III (Hd).

FIG. 2 presents the nucleotide sequence (SEQ ID NO: 1) and deduced amino acid sequence (SEQ ID NO:3) of lipL1. Putative -35 and -10 promotor regions, and ribosome-binding site (RBS) are shown. The putative signal peptidase II cleavage site is indicated by an arrow (↑). The amino acid sequence obtained from the staphylococcal V8 protease digestion of the native protein is underlined. The location of the TAA stop codon is indicated by an asterisk. An inverted repeat is indicated by the horizontal broken arrows. This may function as a rho-independent transcription terminator.

FIG. 4 presents a partial restriction map of the 2.25-kb Eco RI fragment containing the lipL2 gene and strategy for determining the nucleotide sequence. The lipL2 gene is 1065 base pairs in length. The arrows below the map indicate the direction and extent of sequence analysis. Single letters above the map indicate the following restriction enzymes: EcoRI (E), DraI (D), HaeIII (H), ScaI (S), PuvII (P), HindIII (Hd), ClaI (C), HincII (Hc), RsaI (R), and SspI (Ssp).

FIG. 5 presents the nucleotide sequence (SEQ ID NO:4) and deduced amino acid sequence (SEQ ID NO:6) of lipL2. Putative -35 and -10 promotor regions, and ribosome-binding site (RBS) are shown. The putative signal peptidase II cleavage site is indicated by an arrow (↑). The amino acid sequence obtained from the staphylococcal V8 protease digestion of the native protein is underlined. The location of the TAA stop codon is indicated by an asterisk. An inverted repeat is indicated by the horizontal broken arrows. This may function as a rho-independent transcription terminator.

FIG. 7 presents the result of immunoprecipitation experiment of LipL1 with anti-LipL1 antiserum. LipL1 is acylated by L. kirschneri. Lane 1: Whole L. kirschneri intrinsically labeled with [$^3$H] palmitate. Lane 2: L. kirschneri intrinsically labeled with [$^3$H] palmitate, extracted with Triton X-100, and immunoprecipitated with anti-LipL1 antiserum.

FIG. 8 presents the result of immunoprecipitation experiment of LipL2 with anti-LipL2 antiserum. LipL2 is acylated by L. kirschneri. Lane 1: Whole L. kirschneri intrinsically labeled with [$^3$H] palmitate. Lane 2: L. kirschneri intrinsically labeled with [$^3$H] palmitate, extracted with Triton X-100, and immunoprecipitated with anti-LipL2 antiserum. Arrow indicates location of LipL2.

DETAILED DESCRIPTION OF THE INVENTION

Figure 3:
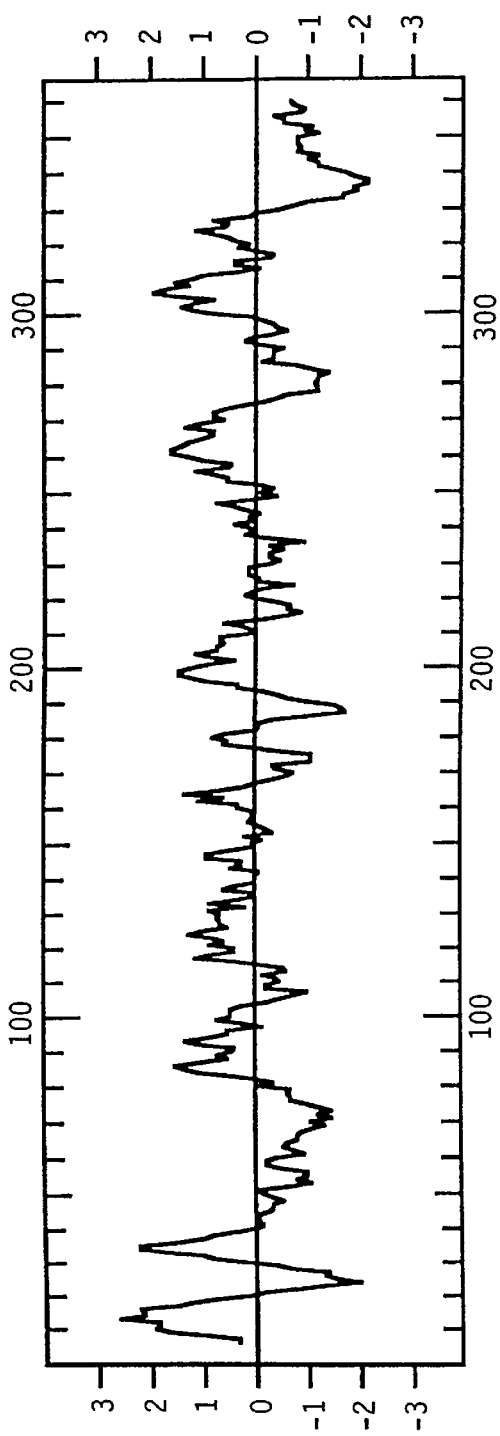
FIG. 3 presents Kyte-Doolittle hydrophobicity plot of LipL1.

The present invention presents two novel leptospiral membrane proteins: LipL1 and LipL2. In particular, these proteins are lipoproteins which are associated with pathogenic strains of Leptospira. LipL1 is of about 35 kDa, and LipL2 is of about 41 kDa. Also disclosed are the method for purifying these proteins from Leptospira, their nucleotide and amino acid sequences, the cloning of the genes encoding the proteins and their recombinant proteins, methods for producing antibodies to these proteins, and the resulting antibodies. These proteins, their immunogenic fragments, and antibodies capable of binding to them are useful for inducing an immune response to pathogenic Leptospira as well as providing a diagnostic target for leptospirosis.

LipL1 and LipL2 are presumed to have an amino-terminal lipid modification based upon sequence analysis of their deduced amino acid sequences. In both cases, the signal peptide is followed by a L-X-Y-C signal peptidase II cleavage site. LipL1 is the most abundant protein found in the detergent phase of Leptospira kirschneri Triton X-114 extracts. Recovery of LipL1 requires the presence of protease inhibitors during detergent solubilization. LipL2 is was identified as a potential membrane protein in surface immunoprecipitation studies, and is also a prominent Triton X-114 detergent phase protein. LipL1 and LipL2 are integral membrane proteins. Recombinant LipL1 and LipL2 fusion proteins were produced in *Escherichia coli* in order to generate specific rabbit antisera. Both lipoproteins are produced by a majority of pathogenic Leptospira species. While the amount of LipL1 produced is variable among Leptospira species, expression of LipL2 is highly conserved. The molecular weights of LipL1 varied from about 35–40 kDa (see, e.g. FIG. 10). The molecular weights of LipL2 were invariant: 41±1 kDa (see, e.g. FIG. 11). LipL1 and LipL2 can be identified in different Leptospira by their immunoreactivity with antibodies raised against the LipL1 and LipL2 described in the "EXAMPLE" section, below. The proteins can be purified from the different Leptospira, and their LipL1 and LipL2 and identified by their immunoreactivity with antisera raised by animals immunized with the LipL1 and LipL2 of the "EXAMPLE", according to the method described in the "EXAMPLE" section. These proteins are useful as pharmaceutical compositions for inducing an immune response to pathogenic Leptospira as well as providing a diagnostic targets for leptospirosis.

The nucleotide and amino acid sequences of LipL1 and LipL2 are shown in FIGS. 2 and 5, and identified as SEQ ID NOS. as follows.

TABLE 1

| | | SEQ ID NO. |
|---|---|---|
| LipL1 | Genomic DNA Sequence (including open reading frame) | 1 |
| LipL1 | Coding DNA Sequence | 2 |
| LipL1 | Protein (including the signal peptide) | 3 |
| LipL2 | Genomic DNA Sequence (including open reading frame) | 4 |
| LipL2 | Coding DNA Sequence | 5 |
| LipL2 | Protein (including the signal peptide) | 6 |

The sequences in Table 1 include both native and synthetic sequences. Unless otherwise modified, the term "protein" as used herein encompasses both native and synthetic polypeptide and peptide. Synthetic protein includes recombinant and chemically synthesized protein. Unless otherwise indicated, "LipL1", and "LipL2" proteins include both their native and synthetic versions.

The nucleotide sequences disclosed in Table 1 and FIGS. 2 and 5 are in the form of DNA. However, based on the disclosed sequences, one skilled in the art could determine their complementary DNA and RNA sequences, and the RNA sequences complementary to the foregoing. Thus, the term "nucleotide sequence" includes both the DNA and RNA sequences. Further, as used in this application and claims, the SEQ ID Nos. and disclosed nucleotide sequences include: (1) the DNA sequences as disclosed, (2) the nucleotide sequences (which may be RNA or DNA) complementary to the disclosed sequences, (3) the corresponding RNA sequences to the listed DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methylcytosine replacing cytosine, and (5) nucleotide sequences that are within a 10% variance to the respective SEQ ID Nos. or disclosed nucleotide sequences.

Since nucleotide codons are redundant, also within the scope of this invention are equivalent nucleotide sequences which include: nucleotide sequences which code for or can be translated into LipL1, LipL2, their protein variants, functional equivalents, or derivatives. These nucleotide sequences may also be used in the practice of the invention.

In addition to the above, LipL1 and LipL2 nucleotide sequences also include: (1) nucleotide sequences that are capable of hybridizing to the coding sequences of the respective nucleotide sequences, under stringent hybridization conditions, and (2) fragments of SEQ ID Nos. 1, 2, 4, and 5 which encode proteins having substantially the same biological characteristics/activities of LipL1 and LipL2, respectively. Preferably, the determinative biological characteristic/activity is the retention of at least one immunoepitope. Preferably, when used in an immunoassay for Leptospira, these proteins are immunoreactive with antibodies directed to Leptospira but not detectably immunoreactive with non-Leptospira specific antibodies found in a biological sample. As herein defined, a "biological sample" can be a biological fluid or tissue sample. Examples of a biological fluid sample include: blood, serum, plasma, tear, milk, urine, and cerebro-spinal fluid. Examples of a biological tissue sample include tissue samples from the liver and kidney and tissue of endothelial origin. A biological sample can also include feces and discharge. Thus, for example, immunohistochemical assay can be conducted on these tissue samples. Preferably, these samples are from mammals, such as humans, wild and domestic mammals. More preferably, these proteins and the immunoassays can additionally distinguish between pathogenic Leptospira and non-pathogenic Leptospira. Alternatively, the fragments of nucleotide sequences can be nucleotide probes of at least 10 nucleotides in length. Preferably, when used in a hybridization assay for Leptospira, under moderate to stringent hybridization condition, these probes do not detectably hybridize to the nucleotide sequences of non-Leptospira organisms which are found in a biological sample. Alternatively, the nucleotide sequences hybridize to at least 10 consecutive nucleotides in the coding sequences of the above listed nucleotide sequences. The nucleotide sequences include a nucleotide sequence which encodes a protein containing at least 8; more preferably, 5 to 6; and most preferably, 4 amino acids. Preferably, the protein is specific to Leptospira or retain one or more biological functions of Leptospira. Most preferably, these nucleotide sequences and the hybridization assays can additionally distinguish between pathogenic Leptospira and non-pathogenic Leptospira.

The terms "LipL1" and "LipL2", as used in relation to proteins are, respectively, as defined above in Table 1 and FIGS. 2 and 5, together with: (1) protein variants containing amino acid sequences that have at least 95% of their amino acids matching the sequences of SEQ ID Nos. 3 and 6, excluding their signal peptides, respectively; (2) the functional equivalents of these proteins and their variants, respectively; and (3) the derivatives, including fragments, of LipL1, LipL2 proteins and their variants, respectively. Preferably, when used in an immunoassay for Leptospira, these proteins are immunoreactive with antibodies directed to Leptospira but not detectably immunoreactive with non-Leptospira specific antibodies found in a biological sample. More preferably, these proteins and the immunoassays can additionally distinguish between pathogenic Leptospira and non-pathogenic Leptospira. Preferably, the proteins are specific to Leptospira or retain one or more biological functions of Leptospira. Thus, preferably, the fragment claimed in this application contains at least one immunogenic epitope of Leptospira and more preferably, of pathogenic Leptospira. More preferably, the fragment is capable of being bound by polyclonal antibodies directed to Leptospira. In the case of antibodies which recognize linear epitopes, they generally bind to epitopes defined by about 3 to 10 amino acids.

Alternatively or additionally, these proteins preferably possess the ability to provoke cellular and/or humoral response in an animal vaccinated with the proteins. More preferably, the cellular and/or humoral response is directed against Leptospira, especially pathogenic Leptospira. Most preferably, animals vaccinated with these proteins are immunized against Leptospirosis or such vaccinations ameliorate the disease in infected animals. The animal is preferably a mammal. More preferably, the animal is a human or a domestic animal. Alternatively, these proteins or their amino acid sequences are preferably derivable from the membrane proteins of Leptospira and are immunoreactive with antibodies raised against the LipL1 or LipL2 disclosed in the "EXAMPLE", below.

The variants can result from, e.g. substitution, insertion, or deletion of the amino acid sequences shown in Table 1. The derivatives of the proteins and their variants, include fragments of these proteins and their immunogenic epitopes. As described above, preferably, too, each variant retains at least one immunoepitope of Leptospira and more preferably, of pathogenic Leptospira. Preferably the immunoepitope is specific to Leptospira and more preferably, to pathogenic Leptospira.

Two amino acid sequences are functionally equivalent if they have substantially the same biological activities such as the ability to provoke cellular and/or humoral response in an animal vaccinated with the proteins. The proteins may be fused to other proteins, for example, signal sequence fusions may be employed in order to more expeditiously direct the secretion of the LipL1 or LipL2 protein. Further, LipL1 may be fused to LipL2. The nucleotide sequences encoding these fusion proteins are also included in the present invention. The heterologous signal replaces the native LipL1 or LipL2 signal, and when the resulting fusion is recognized, i.e. processed and cleaved by the host cell, the LipL1 or LipL2 protein is secreted. Signals are selected based on the intended host cell, and may include bacterial, yeast, insect, and viral sequences.

Substitutional variants of the proteins disclosed herein are those in which at least one residue in the disclosed sequences has been removed and a different residue inserted in its place. Preferably, the amino acid change is conservative. Thus, modifications of LipL1 and LipL2 primary amino acid sequences also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of LipL1 and LipL2. They include variants completely lacking in glycosylation (unglycosylated) and variants having at least one less glycosylated site than the native form (deglycosylated) as well as variants in which the glycosylation has been changed.

The invention also includes a method of producing the membrane lipoproteins of Leptospira using recombinant DNA techniques. Recombinant LipL1 and LipL2 fusion proteins were produced in *Escherichia coli* (*E. coli*). These proteins can be used to immunized a mammal to generate antisera. The genes for the *L. kirschneri* LipL1 and LipL2 proteins were cloned into a plasmid vector which was then used to transform *E. coli*. The molecular weight and amount of LipL2 expressed among pathogenic Leptospira species is highly conserved. On the other hand, though LipL1 is produced by a majority of leptospiral pathogens, the molecular weight and amount of LipL1 produced is variable. There was a strong correlation between leptospiral pathogenicity and reactivity with antisera to LipL1 and LipL2. This is especially so with LipL2 which was detected in all strains of pathogenic Leptospira species of *L. interrogans, L. noguchii, L. kirschneri, L. borgpetersenii, L. santarosai*, and *L. weilii* but not nonpathogenic Leptospira species: *L. biflexa, L. wolbachii*, and *L. inadai*, and the related organism, *Leptonema illini*. LipL1 was detected in most pathogenic Leptospira species but not nonpathogenic Leptospira species: *L. biflexa, L. wolbachii*, and *L. inadai*, and the related organism, *Leptonema illini*. This indicates that LipL1 and LipL2 are not only expressed, but also antigenically conserved among pathogenic Leptospira regardless of species and, therefore, these proteins are excellent vaccine candidates as well as marker antigens for diagnosis of leptospirosis.

Extraction of proteins from whole cells of *L. kirschneri* using nonionic detergent Triton X-114 (TX-114), resulted in the solubilization of a Dumber of proteins, including a detergent phase proteins of the LipL1 and LipL2 proteins. Surface immunoprecipitation using antiserum raised to whole *L. kirschneri*, was used to generate a fraction which was subjected to reducing SDS-polyacrylamide gel electrophoresis. The electrophoresed fraction was then transferred to a sequencing membrane and an N-terminal sequences of the 35 and 41 kDa proteins, respectively, were determined. Based upon the N-terminal amino acid sequence, two degenerate oligonucleotide probes were synthesized for each of the proteins. An *L. kirschneri* genomic DNA library was probed with the oligonucleotides and inserts were identified as containing the coding sequence for LipL1 and LipL2, respectively.

Figure 11:
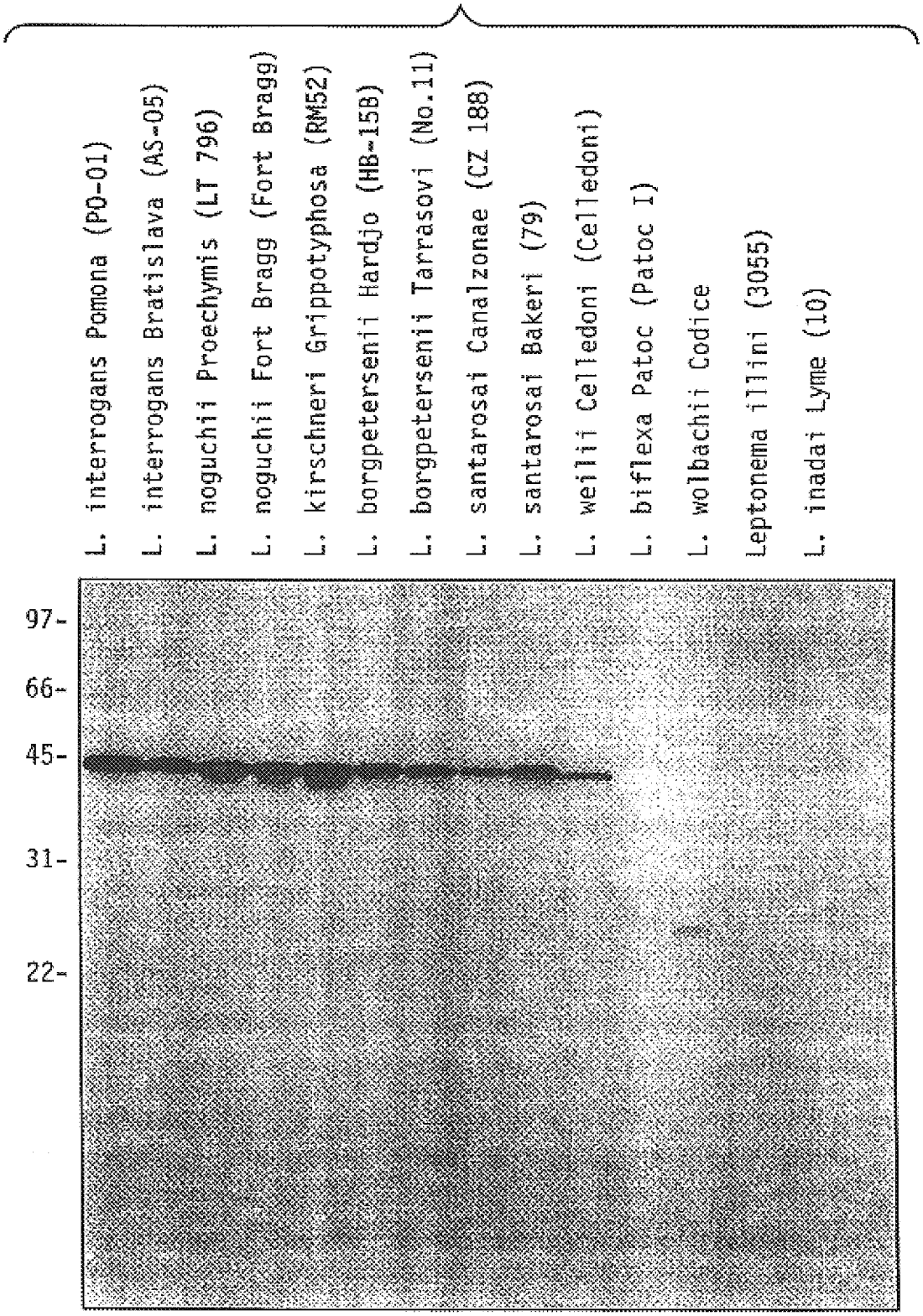
FIG. 11 presents the immunoblot of a panel of Leptospira species using anti-LipL2 antiserum. L. interrogans, L. noguchii, L. kirschneri L. borgpetersenii, L. santarosai, and L. weilii are pathogenic Leptospira species. L. biflexa, L. wolbachii, and L. inadai, are three known nonpathogenic Leptospira species, as is the related organism, Leptonema illini. The locations of the molecular size standards are shown (in kilodaltons) on the left.

Sequence analysis showed that the LipL1 structural gene consists of 1092 bases encoding a protein of 364 amino acids. As expected for a lipoprotein to be exported beyond the inner membrane, the deduced amino acid sequence begins with a 20-residue signal peptide. LipL2 structural gene consists of 1065 bases encoding a protein of 355 amino acids. As expected for a lipoprotein to be exported beyond the inner membrane, the deduced amino acid sequence begins with a 19-residue signal peptide. Immunoblot studies showed that there is a strong correlation between Leptospira pathogenicity and reactivity with antisera to LipL1 and LipL2. Antisera to LipL2 reacted with all strains of pathogenic Leptospira tested, but not with all nonpathogenic strains of Leptospira tested. Antisera to LipL1 reacted with most strains of pathogenic Leptospira tested, but not with all nonpathogenic strains of Leptospira tested; although there was a small amount of reactivity in *L. inadai*, no 41-kDa antigens were detected in *L. biflexa, L. wolbachii*, or *L. illini* (FIG. 11).

The bacterial genes for the LipL1 and LipL2 membrane proteins can be derived from any strain of pathogenic Leptospira. Preferably the proteins are from *Leptospira kirschneri*, serovar grippotyphosa.

The invention provides polynucleotides encoding the Leptospira LipL1 and LipL2 proteins. These polynucleotides include DNA and RNA sequences which encode the protein. As discussed previously, it is understood that all polynucleotides encoding all or a portion of LipL1 and LipL2 are also included herein, so long as they exhibit a function of LipL1 and LipL2, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement {Wallace, et al., *Nucleic Acid Research*, 9:879 (1981)}.

Alternatively, an expression library can be screened indirectly for LipL1 and LipL2 peptides having at least one epitope using antibodies to LipL1 and LipL2. Such antibodies can be either polyclonally or monoclonally derived and used to detect expression product indicative of the presence of LipL1 and LipL2 DNA. Generally, a lambda gt11 library is constructed and screened immunologically according to the method of Huynh, et al. {in *DNA Cloning: A Practical Approach*, D. M. Glover, ed., 1:49 (1985)}.

The development of specific DNA sequences encoding LipL1 and LipL2 can also be obtained by: (1) isolation of a double-stranded DNA sequence from the genomic DNA, and (2) chemical manufacture of a DNA sequence to provide the necessary codons for the polypeptide of interest.

DNA sequences encoding LipL1 and LipL2 can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of the LipL1 and LipL2 outer membrane protein of Leptospira. Prokaryotic hosts may include Gram negative as well as Gram positive bacteria, such as *E. coli, S. typhimurium*, and *Bacillus subtilis*.

A recombinant DNA molecule coding for the LipL1 or LipL2 protein can be used to transform a host using any of the techniques commonly known to those of ordinary skill in the art. Especially preferred is the use of a plasmid containing the LipL1 or LipL2 coding sequence for purposes of prokaryotic transformation. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, the LipL1 or LipL2 sequence may be inserted into a recombinant expression vector. The term "recombinant expression vector" refers to a plasmid, virus or other vehicle known in the art that has been manipulated by insertion or incorporation of LipL1 or LipL2 genetic sequence. Such expression vectors contain a promoter sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported {Heinemann, et al., *Nature*, 340:205 (1989); Rose, et al., *Gene*, 60:237 (1987)}. Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of Leptospira LipL1 and LipL2 in prokaryotic hosts.

Examples of promoters which can be used in the invention are: rec A, trp, lac, tac, and bacteriophage lambda $P_R$, or $P_L$. Examples of plasmids which can be used in the invention are listed in Sambrook, et al., {*Molecular Cloning*, Cold Spring Harbor Laboratories, 1982}.

Antibodies provided in the present invention are immunoreactive with LipL1 or LipL2 protein. These antibodies can be polyclonal antibodies or monoclonal antibodies. Polyclonal antibodies can be produced according to methods known in the art, such as, vaccinating an animal with LipL1 or LipL2 proteins, collecting and purifying the animal's antisera directed against LipL1 or LipL2. Monospecific polyclonal antibodies can also be produced using methods known in the art. Antibody which consists essentially of pooled monoclonal antibodies with different epitopic specificities, as well as distinct monoclonal antibody preparations are also provided. Monoclonal antibodies are made from antigen containing fragments of the protein by methods well known in the art {Kohler, et al., *Nature,* 256:495 (1975); *Current Protocols in Molecular Biology,* Ausubel, et al., ed., (1989)}. For example, monoclonal antibodies can be produced by the method of Kohler and Milstein {*Nature,* 256:495–497 (1975)} by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps. The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel et al., U.S. Pat. No. 4,676,980.

The term antibody, or immunoglobulin, as used in this invention includes intact molecules as well as fragments thereof, such as Fab, F(ab')$_2$, Fv, and single chain antibody (SCA) which are capable of binding an epitopic determinant on LipL1 or LipL2. SCA is a genetically engineered fused single chain molecule containing the variable region of the light chain and the variable region of the heavy chain linked by a suitable polypeptide linker. Methods for making these fragments are known in the art, see e.g., Harlow and Lane, *Antibodies: A Laboratory Manual,* Cold Spring Harbor Laboratory, New York (1988).

As discussed previously, minor modifications of LipL1 and LipL2 primary amino acid sequences may result in proteins which have substantially equivalent function compared to the LipL1 and LipL2 proteins described herein. Such modifications may be deliberate, as by site-directed mutagenesis, or may be spontaneous. All proteins produced by these modifications are included herein as long as LipL1 and LipL2 functions exist.

Isolation and purification of microbially expressed proteins, or fragments thereof, provided by the invention, may be carried out by conventional means including preparative chromatography and immunological separations involving monoclonal or polyclonal antibodies.

The invention extends to any host modified proteins according to the methods described, or modified by any other methods, commonly known to those of ordinary skill in the art, such as, for example, by transfer of genetic material using a lysogenic phage, and which result in a prokaryote expressing the Leptospira gene for LipL1 or LipL2 protein. Prokaryotes transformed with the Leptospira gene encoding the LipL1 or LipL2 protein are particularly useful for the production of proteins which can be used for the immunization of an animal.

In one embodiment, the invention provides a pharmaceutical composition useful for inducing an immune response to pathogenic Leptospira in an animal comprising an immunologically effective amount of LipL1 and/or LipL2 in a pharmaceutically acceptable carrier. The term "immunogenically effective amount," as used in describing the invention, is meant to denote that amount of Leptospira antigen which is necessary to induce in an animal the production of an immune response to Leptospira. LipL1 and LipL2 are particularly useful in sensitizing the immune system of an animal such that, as one result, an immune response is produced which ameliorates the effect of Leptospira infection.

LipL1 and LipL2 proteins i.e., their variants, functional equivalents, and derivatives, which are effective vaccines against Leptospirosis, can be screened for using the methods described in Bolin, C. A., et al., *Am. J. Vet Res.,* 52:1639–1643 (1991) and Bey, R. F., et al., *Infect. Immun.,* 10:1051–1056 (1974). The vaccination methods disclosed in these references can also be used for vaccinating animals with LipL1 and LipL2 proteins.

LipL1 and LipL2 proteins can be administered, alone or in combination, e.g. parenterally by injection, rapid infusion, nasopharyngeal absorption, dermal absorption, and enterally, e.g., orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water.

Besides the inert diluents, such compositions can also include adjuvants, wetting agents, emulsifying and suspending agents, and sweetening, flavoring, and perfuming agents.

For example, recombinant bacteria and viruses expressing LipL1 and/or LipL2 can be used as vaccines in the above compositions, and be administered, e.g. orally. The vaccines can also be added to baits against potential carriers of Leptospira such as rodents so that they will not be infected by Leptospira and be carriers in spreading Leptospira and the disease to humans and other animals, such as domestic animals.

It is also possible for the antigenic preparations containing the LipL1 and/or LipL2 proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete Adjuvants), mineral salts {for example, AlK(SO$_4$)$_2$, AlNa (SO$_4$)$_2$, AlNH$_4$(SO$_4$), silica, alum, Al(OH)$_3$, Ca$_3$(PO$_4$)$_2$, kaolin, and carbon}, polynucleotides (for example, poly IC and poly AU acids), and certain natural substances (for example, wax D from *Mycobacterium tuberculosis,* as well as substances found in *Corynebacterium parvum, Bordetella pertussis,* and members of the genus Brucella).

In another embodiment, a method of inducing an immune response to pathogenic Leptospira in animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira is desirable include any animal susceptible to Leptospira infection. The animals are preferably mammals. Examples of the mammals are: humans, domestic and wild mammals. The domestic mammals include: livestock such as cattle, swine, goats, horses, buffaloes; and pets such as dogs.

Generally, the dosage of LipL1 and/or LipL2 proteins administered to an animal will vary depending on such factors as age, condition, sex and extent of disease, if any, and other variables which can be adjusted by one of ordinary skill in the art.

The antigenic preparations of the invention can be administered as either single or multiple dosages and can vary, e.g. from about 10 ug to about 1,000 ug for the Leptospira LipL1 and/or LipL2 antigen per dose, more preferably from about 50 ug to about 700 ug LipL1 and/or LipL2 antigen per dose, most preferably from about 50 ug to about 300 ug LipL1 and/or LipL2 antigen per dose.

When used for immunotherapy, the antibodies, preferably monoclonal antibodies or SCA, of the invention may be unlabeled or labeled with a therapeutic agent. These agents can be coupled either directly or indirectly to the antibodies of the invention. One example of indirect coupling is by use of a spacer moiety. These spacer moieties, in turn, can be either insoluble or soluble {Diener, et al., *Science,* 231:148 (1986)} and can be selected to enable drug release from the antibody molecule at the target site. Examples of therapeutic agents which can be coupled to the antibodies for immunotherapy are drugs, radioisotopes, lectins, and toxins.

The labeled or unlabeled antibodies can also be used in combination with therapeutic agents such as those described above. Especially preferred are therapeutic combinations comprising the antibody and immunomodulators and other biological response modifiers.

When the antibody is used in combination with various therapeutic agents, such as those described herein, the administration of the antibody and the therapeutic agent usually occurs substantially contemporaneously. The term "substantially contemporaneously" means that the antibody and the therapeutic agent are administered reasonably close together with respect to time. Usually, it is preferred to administer the therapeutic agent before the antibody. For example, the therapeutic agent can be administered 1 to 6 days before the antibody. The administration of the therapeutic agent can be daily, or at any other interval, depending upon such factors, for example, as the nature of the disorder, the condition of the patient and half-life of the agent.

The dosage ranges for the administration of antibodies are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary, e.g., from about 0.1 mg/kg to about 2000 mg/kg, preferably about 0.1 mg/kg to about 500 mg/kg, in one or more dose administrations daily, for one or several days. Generally, when the antibodies are administered conjugated with therapeutic agents, lower dosages, comparable to those used for in vivo diagnostic imaging, can be used.

The antibodies can be administered parenterally by injection or by gradual perfusion over time. The antibodies can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases, preferably isolated or substantially pure, and the like.

An animal may also be vaccinated using the disclosed, preferably isolated or in substantially pure composition, nucleic acid sequences, their mutagenized sequences or fragments thereof, which may be directly injected or incorporated into a plasmid and injected into the animal. The nucleic acid sequences may be mixed with a pharmaceutically acceptable carrier prior to injection. The injections may be by means of a gene gun, such as described in Yang, N.-S. et al., *Gene Therapy via Particle Bombardment: Applications of the Accell Gene Gun,* in *Gene Therapeutics: Methods and Applications of Direct Gene Transfer,* Wolff, J. A., ed., Birkhauser, USA (1994).

In a further embodiment, the invention provides a method of detecting a pathogenic Leptospira-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for LipL1 or LipL2 may be used to detect the presence of the respective LipL1 or LipL2 protein (using antibody) or polynucleotide (using nucleic acid probe) in biological samples. Any specimen containing a detectable amount of LipL1 or LipL2 antigen or polynucleotide can be used. Preferred specimens of this invention are a biological fluid or tissue sample. Preferred examples of a biological fluid sample include: blood, serum, plasma, tear, milk, urine, and cerebro-spinal fluid. Preferred examples of a biological tissue sample include tissue samples from the liver and kidney and tissue of endothelial origin.

When the cell component is nucleic acid, it may be necessary to amplify the nucleic acid prior to binding with a Leptospira specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, LipL1 or LipL2 protein can be used to detect antibodies to the respective LipL1 or LipL2 protein in a specimen. The LipL1 and LipL2 of the invention is particularly suited for use in immunoassays in which they can be utilized in liquid phase or bound to a solid phase carrier. In addition, LipL1 and LipL2 used in these assays can be detectably labeled in various ways.

Examples of immunoassays which can utilize the LipL1 and LipL2 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the LipL1 or LipL2 of the invention can be done utilizing immunoassays which run in either the forward, reverse, or simultaneous modes, including immunohistochemical assays on biological samples. The concentration of LipL1 and LipL2 which is used will vary depending on the type of immunoassay and nature of the detectable label which is used. However, regardless of the type of immunoassay which is used, the concentration of LipL1 and LipL2 utilized can be readily determined by one of ordinary skill in the art using routine experimentation.

The LipL1 and LipL2 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding LipL1 and LipL2 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to LipL1 or LipL2 of the invention may be present in various biological samples. Any sample containing a detectable amount of antibodies to LipL1 or LipL2 can be used. Preferred specimens of this invention are: a biological fluid or tissue sample. Preferred examples of a biological fluid sample include: blood, serum, plasma, tear, milk, urine, and cerebro-spinal fluid. Preferred examples of a biological tissue sample include tissue samples from the liver and kidney and tissue of endothelial origin.

The antibodies of the invention, preferably monoclonal antibodies and SCA, directed toward LipL1 or LipL2, are also useful for the in vivo detection of antigen. The detectably labeled antibody is given in a dose which is diagnostically effective. The term "diagnostically effective" means that the amount of detectably labeled monoclonal antibody is administered in sufficient quantity to enable detection of Leptospira LipL1 or LipL2 antigen for which the antibodies are specific.

The concentration of detectably labeled antibody which is administered should be sufficient such that the binding to those cells, body fluid, or tissue having LipL1 and/or LipL2 is detectable compared to the background. Further, it is desirable that the detectably labeled antibody be rapidly cleared from the circulatory system in order to give the best target-to-background signal ratio.

As a rule, the dosage of detectably labeled antibody for in vivo diagnosis will vary depending on such factors as age, sex, and extent of disease of the subject. The dosage of antibody can vary, e.g., from about 0.001 mg/m$^2$ to about 500 mg/m$^2$, preferably 0.1 mg/m$^2$ to about 200mg/m$^2$, most preferably about 0.1 mg/m$^2$ to about 10 mg/m$^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The antibodies, preferably monoclonal antibodies and SCA, of the invention can also be used to monitor the course of amelioration of Leptospira associated disorder. Thus, by measuring the increase or decrease of Leptospira LipL1 and/or LipL2 proteins or antibodies to LipL1 and/or LipL2 proteins present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a LipL1 and/or LipL2 binding reagents, such as an antibody. A second container may further comprise LipL1 and/or LipL2 proteins. The constituents may be present in liquid or lyophilized form, as desired.

In the above discussion, the diagnostic tests, e.g. nucleic acid hybridization assays or immunoassays, may test for either or both LipL1 and LipL2. Alternatively, they may consist of panel tests which test for both LipL1 and LipL2 proteins or nucleic acid sequences, in combination with other proteins or nucleic acid sequences specific for Leptospira, in particular pathogenic Leptospira, such as OmpL1 {Haake, D. A., et al., *J. Bacteriol.*, 175:4225–4234 (1993); U.S. patent application Ser. No. 08/040,747, "Cloned Leptospira Outer Membrane Protein" to Haake, D. A., et al., filed on Mar. 31, 1993} and OmpL2 {U.S. patent application Ser, No. 08/249,013, "Cloned Leptospira Outer Membrane Protein" to Haake, D. A., et al., filed on May 25, 1994}. Similarly, the compositions, e.g. for immunoassays or vaccinations, may consist of LipL1 or LipL2, singly. Alternatively, they may consist of a cocktail containing both LipL1 and LipL2, or these proteins in combination with other proteins specific for Leptospira, in particular pathogenic Leptospira, such as OmpL1 and OmpL2. The antibody compositions may consist of antibodies specific to LipL1 or LipL2. Alternatively, they may consist of a cocktail containing antibodies to LipL1 and LipL2, or to these proteins and other proteins specific for Leptospira, in particular pathogenic Leptospira, such as OmpL1 and OmpL2. The hybridization assays are preferably run at moderate to stringent conditions. The immunoassays are preferably conducted under conditions of reduced non-specific binding. Thus, the test kits and methods using these compositions are varied accordingly.

The following examples are intended to illustrate but not limit the invention. While they are typical of those that might be used, other procedures known to those skilled in the art may alternatively be used.

EXAMPLE

The following example describes the identification, cloning, sequencing, and characterization of LipL1 and LipL2. There was a strong correlation between leptospiral pathogenicity and reactivity with antisera to LipL1 and LipL2.

Materials and Methods

Leptospiral strains. Virulent and culture-attenuated *Leptospira kirschneri*, strain RM52, (formerly *L. alstoni*) were received from C. A. Bolin (National Animal Disease Center, Agricultural Research Service, U.S. Department of Agriculture, Ames, Iowa). This strain was originally isolated from material submitted to the Veterinary Diagnostic Laboratory at Iowa State University during an outbreak of swine abortion in 1983 {Thiermann, A. B., et al, *Ann. Proc. Amer. Assn. Veterinary Laboratory Diagnosticians*, 27:233–244 (1984)}. Samples of the isolate were either stored in liquid nitrogen {Alexander, A. D., et al., *International J. System. Bacteriol.*, 22:165–169 (1972)} or passaged weekly or biweekly in liquid EMJH medium {Johnson, R. C., et al., *J Bacteriol.*, 94:27–31 (1967)}. The virulent strain had been passaged less than five times. The attenuated strain has been passaged more than 200 times since 1983. Other Leptospira species were kindly supplied by C. A. Bolin.

*Escherichia coli*. *E. coli* DH5α (supE44, ΔlacU169, [φ80, lacZ, ΔM15], hsdR17, recA1, endA1, gyrA96, thi-1, relA1) was used as the host strain for transformations of recombinant DNA. *E. coli* strain PLK-F' (recA, lac, mcrA, mcrB, hsdR, gal, supE [F' proAB, lacIqZΔM15, Tn10 (tet$^R$)]) was used as the host strain for infection with the λzap II vector (Stratagene, San Diego, Calif.). *E. coli* strain JM109 (recA1, supE44, endA1, hsdR17, gyrA96, relA1, thiΔ[lacproAB], F'[traD36, proAB$^+$, lacI$^q$, lacZΔM15]) was used as the host strain for the pRSET expression vector (Invitrogen Corp., San Diego, Calif.).

SDS-PAGE and immunoblotting. Samples for sodium dodecyl sulfate polyacrylamide gel electrophoresis (SDS-PAGE) were solubilized in final sample buffer (FSB) composed of 62.5 mM Tris hydrochloride (pH 6.8), 10% glycerol, 5% 2-mercaptoethanol, 2% SDS, and 8 M urea, unless otherwise noted. Proteins were separated on a 10% gel with a discontinuous buffer system {Laemmli, U. K., *Nature* (London), 227:680–685 (1970)} and transferred to nitrocellulose (Schleicher & Schuell Inc., Keene, N.H.) for immunoblotting. For antigenic detection on immunoblots, the nitrocellulose was blocked with 5% nonfat dry milk in Phosphate Buffered Saline-0.1% Tween-20 (PBS-T), incubated for one hour with antiserum diluted 1:5000 (unless otherwise noted) in PBS-T, and probed with Donkey anti-rabbit antiserum conjugated to horseradish peroxidase (Amersham Corporation, Arlington Heights, Ill.). Antigen-antibody binding was detected using the Enhanced Chemiluminescence System (ECL, Amersham). Blots were incubated in ECL reagents for one minute and then exposed to XAR-5 film (Fuji Medical Systems, Stamford, Conn.).

Triton X-114 Extraction of Leptospira. Culture-attenuated *L. kirschneri* was extracted with 1% Triton X-114 by a modification of the method described previously {Haake, D. A., et al., *Infection & Immunity*, 59:1131–40 (1991)}. In brief, culture-attenuated *L. kirschneri* were washed twice in phosphate buffered saline, 5 mM MgCl$_2$, and extracted in the presence of 1% protein grade Triton X-114 (Calbiochem, La Jolla, Calif.), 10 mM Tris pH 8, 1 mM PMSF, 1 mM iodoacetamide, and 10 mM EDTA at 4° C. The insoluble material was removed by centrifugation at 17,000×g for ten minutes. The Triton X-114 concentration of the supernatant was increased to 2%. Phase separation was performed by warming the supernatant to 37° C. and subjecting it to centrifugation for 10 min at 2,000×g. The detergent and aqueous phase proteins were precipitated with acetone.

N-terminal Amino Acid Sequencing. Lipoproteins were isolated by SDS-PAGE and digested with Staphylococcal V8 protease. The polypeptide fragments were subjected to SDS-PAGE, transferred to Trans-Blot PVDF Protein Sequencing Membrane (Bio-Rad, Richmond, Calif.), and submitted to the University of California, Los Angeles (UCLA) Protein Microsequencing Facility. N-terminal amino acid sequence analysis was performed on a Porton 1090-E gas-phase sequenator with on line detection of PTH amino acids.

Southern blot analysis. *L. kirschneri* genomic DNA was prepared by the method of {Yelton, D. B., et al., *Gene*, 28:147–152 (1984)}. Leptospiral DNA was digested with Eco RI and electrophoresed in a 1.0% agarose gel. Following depurination, denaturation, and neutralization, the DNA was transferred to a nylon filter (Zeta-Probe, Bio-Rad) by the method of Southern {Sambrook, J., et al., Molecular Cloning: A Laboratory Manual, 2nd ed., Cold Spring Harbor Laboratory, Cold Spring Harbor, N.Y. (1989)}. Filters were baked for 2 hours at 80° C. under vacuum and prehybridized for 3 hours at 37° C. in buffer containing 6×SSC, 1×Denhardt's solution, 0.05% Sodium pyrophosphate, 0.5% SDS, and 100 μg/ml of denatured salmon sperm DNA. The filters were then hybridized overnight at 37° C. with radiolabeled oligonucleotides.

Two degenerate oligonucleotide probes, each twenty base pairs in length, were synthesized based upon the N-terminal amino acid sequences of the lipoprotein fragments. Synthetic oligonucleotides were prepared using an automated oligonucleotide synthesizer (380B, Applied Biosystems, Inc., Foster City, Calif.). For degenerate oligonucleotide probes, the filters were washed at 47° C. in 3.0 M tetramethylammonium chloride (Aldrich Chemical Company, Milwaukee, Wis.), 50 mM Tris pH 8.0, 2.0 mM EDTA, 1.0% SDS as previously described {Wood, W. I., et al., *Proc. Natl. Acad. Sci. USA,* 82:1585–1588 (1985)}. Degenerate oligonucleotide probes were end-labeled with $^{32}$P-dATP by T4 polynucleotide kinase (Promega Corp., Madison, Wis.).

Cloning and sequencing of the lipL1 and lipL2 genes. Standard recombinant DNA procedures were performed as described {Sambrook, J., et al., Molecular Cloning: A Laboratory Manual, 2nd ed., Cold Spring Harbor Laboratory, Cold Spring Harbor, N.Y. (1989)}. Restriction endonuclease digests were performed as recommended by the suppliers (New England Biolabs, Inc., Beverly, Mass. and Promega). Eco RI fragments of *L. kirschneri* genomic DNA were ligated into the Lambda Zap II vector (Stratagene). The ligated DNA was packaged with Gigapack II Gold packaging extract (Stratagene) and stored in 0.3% chloroform at 4° C. The plaque titer was determined by infecting *E. coli* PLK F' (Stratagene). Plaques were plated, transferred to filters in duplicate, and processed as previously described {Sambrook, J., et al., Molecular Cloning: A Laboratory Manual, 2nd ed., Cold Spring Harbor Laboratory, Cold Spring Harbor, N.Y. (1989)}. The same oligonucleotide probe hybridization and washing conditions were used as described above for Southern hybridization. Recombinant pBluescript SK(-) clones were recovered from phage producing positive plaques by in vivo excision according to the manufacturer. After restriction mapping, appropriate DNA fragments were subcloned into pBluescript KS and sequenced at the UCLA Core DNA Sequencing Facility by the dideoxy chain termination method with fluorescein-labeled dideoxy nucleotides (Applied Biosystems Inc.).

DNA sequence analysis. DNA sequence information was analyzed by the DNA Strider program {Marck, C., *Nucleic Acids Res.,* 16:1829–1836 (1988)}. Homology searches were performed with the BLAST, FASTA and Profile Search programs which are found in the University of Wisconsin Genetics Computer Group (GCG), Inc. (Genetics Computer Group, Inc., Madison, Wis.) package, ver. 7.0 {Devereux, J. et al., *Nucl. Acids Res.,* 12:387–395 (1984)}. Secondary structure predictions were based upon analysis using the programs PEPPLOT and PLOTSTRUCTURE which are also found in the GCG package.

Immunization with His6-LipL1 fusion protein. Lacking a convenient restriction endonuclease site near the aminoterminus of the mature LipL1 protein, the polymerase chain reaction was used to amplify the portion of the lipL1 gene encoding the mature protein beginning with the first residue after the aminoterminal cysteine. The 5' oligonucleotide contained the nucleotide sequence coding for the six amino acids following the aminoterminal cysteine of mature LipL1, including a BglII restriction endonuclease site (underlined): 5'-TTA ACG ACA TCT AAA AGT GAC GAC GAT GAT-3' (SEQ ID NO: 13). The 3' oligonucleotide consisted of a 24 base pair nucleotide sequence beginning 133 base pairs downstream of the lipL1 stop codon: 5'-CAT GAT AAA AAT TGA AAA TGA TTC AAG AAT-3' (SEQ ID NO:14). The nucleotide sequence between the lipL1 stop codon and the 3' oligonucleotide sequence includes a unique HindIII restriction endonuclease site. *L. kirschneri* genomic DNA, prepared as described previously {Yelton, et al., *Gene,* 28:147–152 (1984)} was used as template. The 1144 base pair BglII-HindIII fragment of the amplified lipL1 gene was ligated into pRSETb (Invitrogen) digested with BglII and Hind III. The resulting construct pRSETb-JR2, was transformed into *E.* coli JM109 (Invitrogen). Expression of the His6-LipL1 fusion protein was achieved by isopropylthio-b-D-galactoside (IPTG, Sigma Chemical Co., St. Louis, Mo.) induction followed by infection with M13/T7 phage containing the T7 polymerase gene driven by the *E. coli* lac promoter. The His6LipL1 fusion protein was solubilized in 6M guanidine and purified by affinity chromatography using Ni$^{2+}$-NTA-Agarose (Qiagen) and dialyzed in 20 mM Tris, pH 8, 50 mM NaCl, and 10% glycerol. Roughly 30 micrograms of His6-LipL1 was mixed with Freund's complete adjuvant and inoculated subcutaneously and intramuscularly into a New Zealand White male rabbit. The secondary immunization used roughly 30 micrograms of purified His6-LipL1 fusion protein in Freund's incomplete adjuvant. The rabbit was bled two weeks after the secondary immunization.

Immunization with His6-LipL2 fusion protein. An 842 base pair HaeIII-ClaI fragment of the lipL2 gene, encoding the aminoterminal three-fourths of the protein, was ligated into pRSETa (Invitrogen) digested with PvuII and ClaI. The resulting construct pRSETa-800HC, was transformed into *E. coli* JM109 (Invitrogen). Expression of the His6-LipL2 fusion protein was achieved by isopropylthio-b-D-galactoside (IPTG, Sigma) induction followed by infection with M13/T7 phage containing the T7 polymerase gene driven by the *E. coli* lac promoter. The His6-LipL2 fusion protein was solubilized in 6M guanidine and purified by affinity chromatography using Ni$^{2+}$-NTA-Agarose (Qiagen) and dialyzed in 20 mM Tris, pH 8, 50 mM NaCl, and 10% glycerol. Roughly 400 micrograms of His6-LipL2 was mixed with Freund's complete adjuvant and inoculated subcutaneously and intramuscularly into a New Zealand White male rabbit. The secondary immunization used roughly 450 micrograms of purified His6-LipL2 fusion protein in Freund's incomplete adjuvant. The rabbit was bled two weeks after the secondary immunization.

Results

Design of oligonucleotide probes and cloning of the lipL1 gene. Staphylococcal V8 protease digestion of LipL1 resulted in fragments of with molecular masses of2 1-, 9-, and 5-kDa in size. N-terminal amino acid sequence analysis of the 21 -kDa fragment revealed the sequence YFGKTV-LVRPSEQAKQKQIVLL (SEQ ID NO:7). A 23 base-pair oligonucleotide probe with 256-fold degeneracy, GA(AG)CA(AG)GC(AGCT)AA(AG)CA(AG)AA(AG)CA(AG)AT (SEQ ID NO:8), was designed based upon the portion of sequence EQAKQKQI (SEQ ID NO:9). The oligonucleotide probe independently identified a 2.3 kb Eco RI fragment by Southern hybridization of the *L. kirschneri* genome. The 2.3 kb Eco RI fragment was cloned from a partial lambda ZAP II (Stratagene) library of *L. kirschneri* genomic DNA as described previously {Haake, D. A., et al., *J. Bacteriol.,* 175:4225–4234 (1993)}.

Design of oligonucleotide probes and cloning of the lipL2 gene. Staphylococcal V8 protease digestion of LipL2 resulted in fragments of with molecular masses of21-, and 17-kDa in size. N-terminal amino acid sequence analysis of the 17-kDa fragment revealed the sequence ASLSLTGIT-KNRAKIGNL (SEQ ID NO: 10). A 20 base-pair oligonucleotide probe with 864-fold degeneracy, AC(TAG)GG(TAG)AT(CAT)AC(TCAG)AA(AG)AA(TC)(AC)G (SEQ ID NO:11), was designed based upon the portion of sequence TGITKNR (SEQ ID NO:12). Codon bias was used for the first threonine residue and glycine residue based upon the low GC content of Leptospira spp. {Johnson, et al., Family II. Leptospiraceae, In N. R. Krieg and J. G. Holt (ed.) Bergey's manual of systematic bacteriology, Vol. 1, pp. 62–67, The Williams & Wilkins Co., Baltimore, (1984)}. The oligonucleotide probe independently identified a 2.3 kb Eco RI fragment by Southern hybridization of the *L. kirschneri* genome. The 2.3 kb Eco RI fragment was cloned from a partial lambda ZAP II (Stratagene) library of *L. kirschneri* genomic DNA as described previously {Haake, D. A., et al., *J. Bacteriol.*, 175:4225–4234 (1993)}.

Sequence analysis of the lipL1 gene. Restriction mapping, Southern blot analysis, and DNA sequencing revealed that the entire lipL1 gene is encoded by the 2.3 kb Eco RI fragment (FIG. 1). An intact open reading frame was identified 430 base pairs downstream from the Eco RI site. The lipL1 structural gene consists of 1092 bases encoding a protein of 364 amino acids. *E. coli*-like-35 (TTGACC) and -10 (TATTAT) promoter regions, and a consensus ribosome-binding site (AAGAGG) are present upstream from the initiation codon (FIG. 2). As expected for a lipoprotein, the deduced amino acid sequence begins with a 20 residue signal peptide, represented by the N-terminal peak on the hydrophobicity plot (FIG. 3). The LipL1 sequence conforms to the rules established for procaryotic lipoprotein signal peptides {Pugsley, A. P., *Microbiol. Rev.*, 57:50–108 (1993); Hayashi, S., et al., *J. Bioenerg. Biomembr.*, 22:451–471 (1990)}. The LipL1 signal peptide has a basic amino-terminal region (including arginines at positions 2 and 3), a hydrophobic core (amino acids 8 through 20), and a carboxyterminal Leu-X-Y-Cys signal peptidase II cleavage site. Staphylococcal V8 protease is known to cleave peptides following acidic amino acids. Immediately following the glutamic acid residue 174 is a sequence that is identical in 20 of 22 amino acids to the sequence obtained by N-terminal amino acid sequence analysis of the native protein (FIG. 2). After cleavage of the 20-amino-acid signal peptide by leptospiral signal peptidase II, the mature polypeptide would have a predicted molecular mass of 35.3 kDa. Thirty base pairs downstream from the termination codon is an inverted repeat which may function as a rho-independent transcription terminator (FIG. 2). Data base searching using the FASTA, BLAST, and Profile Search programs failed to reveal significant amino acid homologies. There are two unusual features of the deduced amino acid sequence of LipL1. The first is a series of six consecutive aspartic acid residues beginning three residues after the N-terminal cysteine of the mature protein. The second unusual feature is an abundance of alanine residues. In the mature LipL1 protein, 55/344 residues are alanines, 25 of which are arranged in pairs or triplets.

Figure 6:
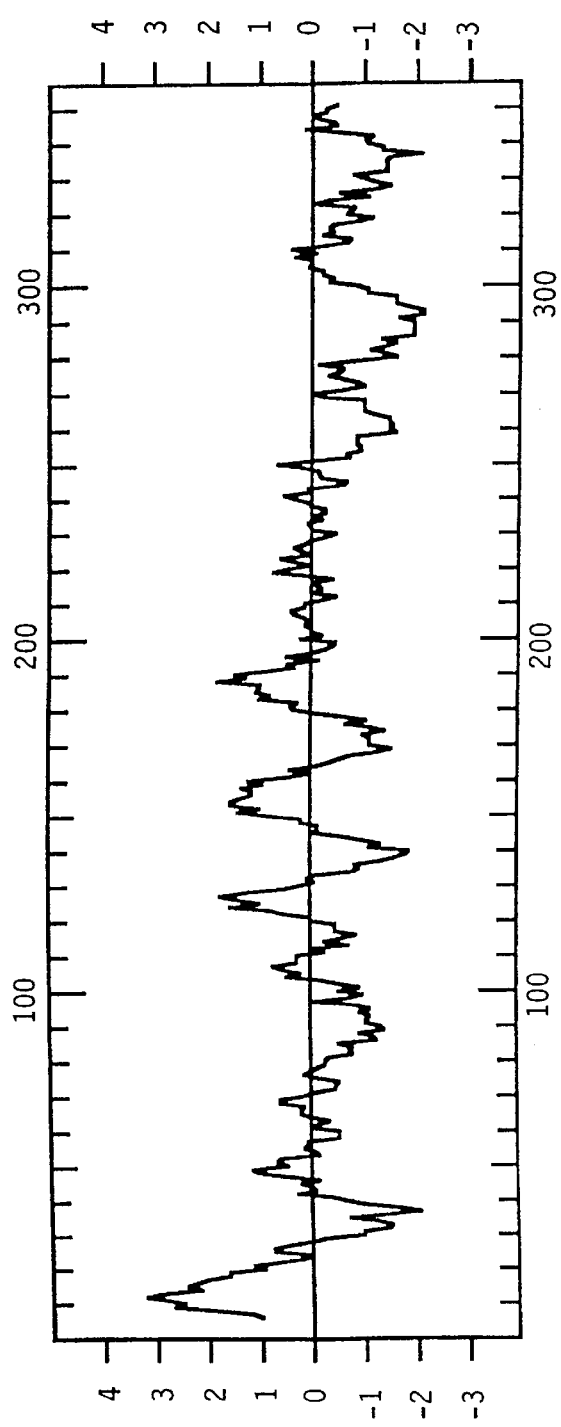
FIG. 6 presents the Kyte-Doolittle hydrophobicity plot of LipL2.

Sequence analysis of the lipL2 gene. Restriction mapping, Southern blot analysis, and DNA sequencing revealed that the entire lipL2 gene is encoded by the 2.25 kb EcoRI fragment (FIG. 4). An intact open reading frame was identified 170 base pairs downstream from the EcoRI site. The lipL2 structural gene consists of 1065 bases encoding a protein of 355 amino acids. *E. coli*-like-35 (TTGACA) and -10 (TTAAAT) promoter regions, and a consensus ribosome-binding site (AGGA) are present upstream from the initiation codon (FIG. 5). As expected for a lipoprotein, the deduced amino acid sequence begins with a 19 residue signal peptide, represented by the N-terminal peak on the hydrophobicity plot (FIG. 6). The LipL2 sequence conforms to the rules established for procaryotic lipoprotein signal peptides {Pugsley, A. P., *Microbiol. Rev.*, 57:50–108 (1993); Hayashi, S., et al., *J. Bioenerg. Biomembr.*, 22:451–471 (1990)}. The LipL2 signal peptide has a basic amino-terminal region (including an arginine at position 2, and a lysine at position 3), a hydrophobic core (amino acids 4 through 17), and a carboxyterminal Leu-X-Y-Cys signal peptidase II cleavage site. Staphylococcal V8 protease is known to cleave peptides following acidic amino acids. Immediately following the glutamic acid residue 104 is a sequence of 18 amino acids that is 100% identical to the sequence obtained by N-terminal amino acid sequence analysis of the native protein (FIG. 5). After cleavage of the 19-amino-acid signal peptide by leptospiral signal peptidase II, the mature polypeptide would have a predicted molecular mass of 36.8 kDa. Twenty-seven base pairs downstream from the termination codon is an inverted repeat which may function as a rho-independent transcription terminator (FIG. 5). Data base searching using the ASTA, BLAST, and Profile Search programs failed to reveal significant amino acid homologies. However, alignment of the LipL2 amino acid sequence with the OspA sequence of *B. burgdorferi* using the GAP program revealed a region of 53% identity in the carboxyterminal 15 residues.

*L. kirschneri* acylates LipL1 and LipL2. Intrinsic labeling of culture-attenuated *L. kirschneri* with [$^3$H] palmitate resulted in the incorporation of label in leptospiral glycolipid (lipopolysaccharide-like substance), which appears diffusely at the bottom of the whole organism lane, as well as at least ten proteins which form discrete bands in the whole organism lane (FIGS. 7 and 8). Immunoprecipitation experiments with anti-LipL1 antiserum (FIG. 7) and anti-LipL2 antiserum (FIG. 8) confirm that these two proteins are the second and third smallest lipoproteins, respectively, identified in these autoradiographs.

Figure 9:
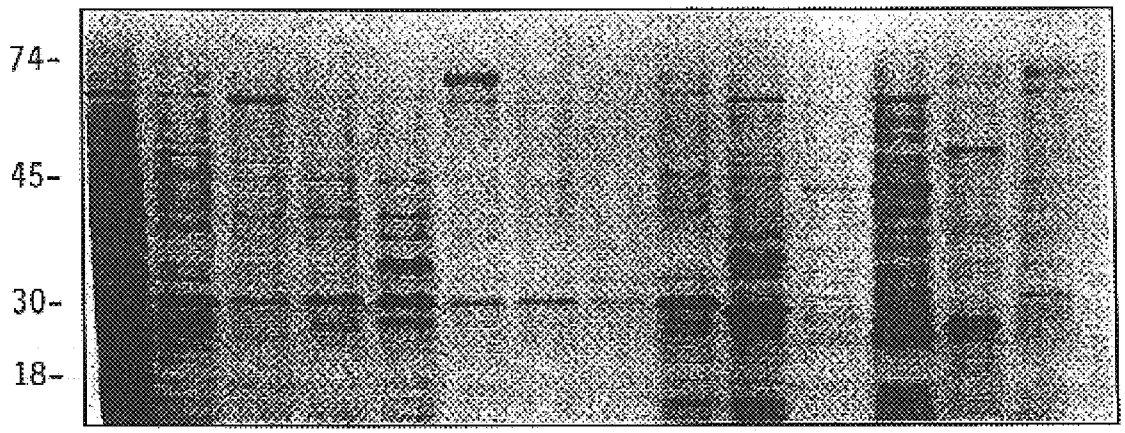
FIG. 9 presents Coomassie blue stained SDS-PAGE gel of a panel of Leptospira species. L. interrogans, L. noguchii, L. kirschneri, L. borgpetersenii, L. santarosai, and L. weilii are pathogenic Leptospira species. L. biflexa, L. wolbachii, and L. inadai, are three known nonpathogenic Leptospira species, as is the related organism, Leptonema illini. The locations of the molecular size standards are shown (in kilodaltons) on the left.
Figure 10:
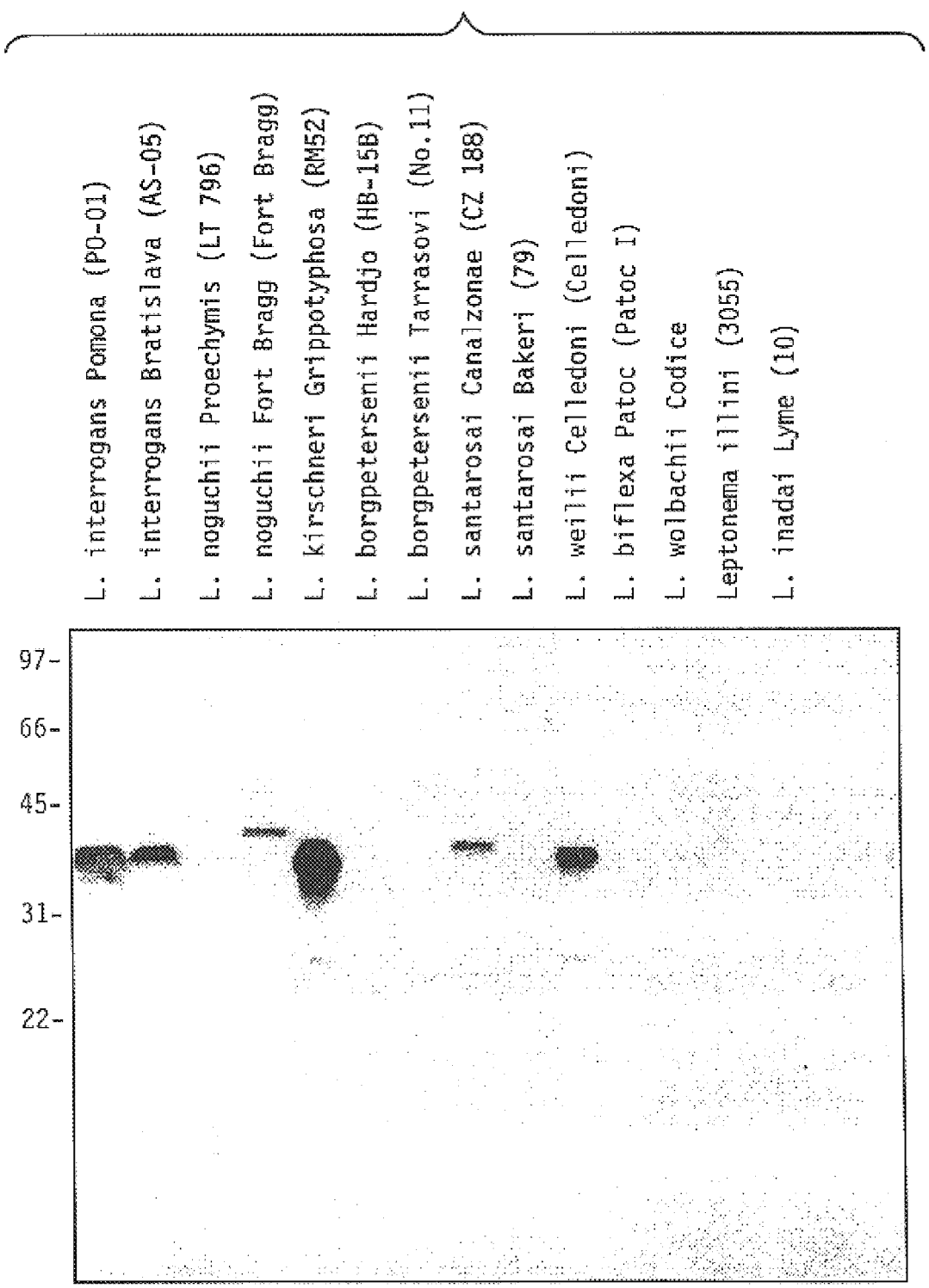
FIG. 10 presents the immunoblot of a panel of Leptospira species using anti-LipL1 antiserum. L. interrogans, L. noguchii, L. kirschneri, L. borgpetersenii, L. santarosai, and L. weilii are pathogenic Leptospira species. L. biflexa, L. wolbachii, and L. inadai, are three known nonpathogenic Leptospira species, as is the related organism, Leptonema illini. The locations of the molecular size standards are shown (in kilodaltons) on the left.

Expression of LipL1 and LipL2 in Leptospira species. To address the level and distribution of LipL1 and LipL2 expression, immunoblot analysis was performed on a panel of Leptospira species, using specific antisera. FIG. 10 shows that while LipL1 is produced by a majority of leptospiral pathogens, the molecular weight and amount of LipL1 produced is extremely variable. The *L. kirschneri* RM52 strain was found to produce the most LipL1 among the Leptospira species tested. Comparison of the LipL1 immunoblot with the Coomassie blue stained gel (FIG. 9) shows that the differences observed cannot be accounted for entirely on the basis of preferential reactivity of the LipL1 antiserum with the source strain. In contrast, FIG. 11 shows that the molecular weight and amount of LipL2 expressed among pathogenic Leptospira species is highly conserved. LipL2 is expressed in relatively the same amount by all leptospiral pathogens tested.

There was a strong correlation between leptospiral pathogenicity and reactivity with antisera to LipL1 and LipL2. LipL1 was not detected in *L. biflexa, L. inadai*, or *L. wolbachii*, three nonpathogenic species of Leptospira, nor in the related nonpathogen, *Leptonema illini* (FIG. 10). Although there was a small amount of reactivity in *L. inadai*, no 41-kDa antigens were detected in *L. biflexa, L. wolbachii*, or *L. illini* (FIG. 11).

Figure 13:
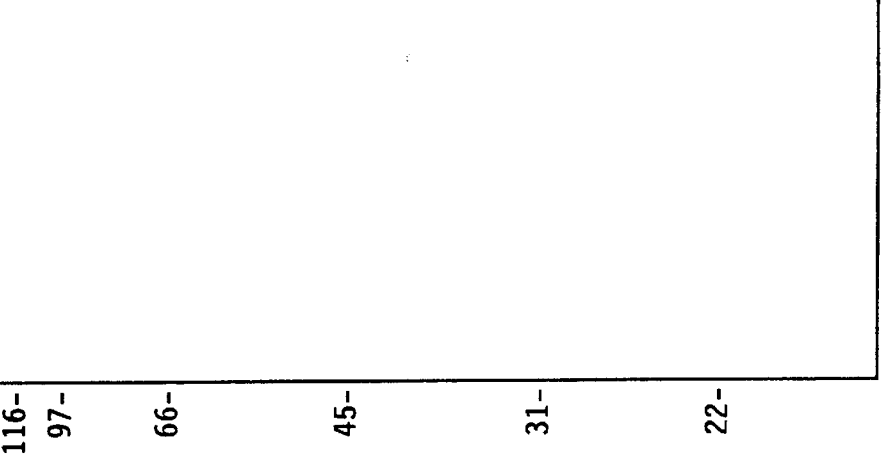
FIG. 13 shows that LipL2 partitions selectively into the Triton X-114 detergent phase. It presents an immunoblot of culture-attenuated L. kirschneri organisms probed with anti-LipL2 antiserum. Fractions analyzed were the whole organism (W) and Triton X-114-insoluble pellet (P), aqueous phase (A), and detergent phase (D) material. The locations of the molecular size standards are shown (in kilodaltons) on the left.
Figure 12:
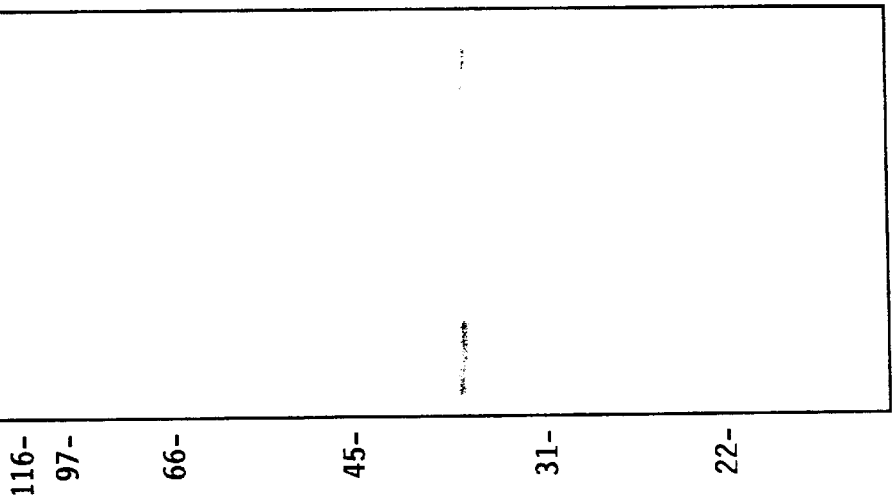
FIG. 12 shows that LipL1 partitions selectively into the Triton X-114 detergent phase. It presents an immunoblot of culture-attenuated L. kirschneri organisms probed with anti-LipL1 antiserum. Fractions analyzed were the whole organism (W) and Triton X-114-insoluble pellet (P), aqueous phase (A), and detergent phase (D) material. The locations of the molecular size standards are shown (in kilodaltons) on the left.

Behavior of LipL1 and LipL2 during Triton X-114 extraction and phase partitioning. Both LipL1 and LipL2 selectively partitioned into the Triton X-114 detergent phase (FIGS. 12 and 13), a known characteristic of lipoproteins. LipL1 was completely extracted in 1% Triton X-114, as demonstrated by complete removal from the detergent insoluble pellet (FIG. 12). By contrast, residual LipL2 reactivity was found in the insoluble pellet (FIG. 13), a pattern that was previously observed for OmpL1 {Haake, D. A., et al., *J. Bacteriol.*, 175:4225–4234 (1993)}.

Evidence suggesting LipL1 and LipL2 are two leptospiral lipoproteins. Several lines of evidence support the conclusion that these proteins are lipoproteins. First of all, both proteins were found to be blocked to N-terminal amino acid sequencing until subjected to Staphylococcal V8 protease digestion. Secondly, analysis of their deduced amino acid sequences reveals a signal peptide followed by a L-X-Y-C signal peptidase II cleavage site. Thirdly, LipL1 and LipL2 are labeled by [³H] palmitate intrinsic labeling of *L. kirschneri*. Lastly, both LipL1 and LipL2 selectively partition into the Triton X-114 detergent phase.

Although LipL1 and LipL2 both partition into the Triton X-114 detergent phase, they appear to be distinct from the 31-kDa protein identified by Zuerner, et al. {Zuerner, et al., *Microbial. Pathogenesis,* 10:311–322 (1991)} in *L. interrogans* serovar Pomona. Antisera to LipL1 and LipL2 reacted with *L. interrogans* serovar Pomona antigens that were clearly larger than 1-kDa (FIGS. 10 and 11).

The foregoing is meant to illustrate, but not to limit, the scope of the invention. Indeed, those of ordinary skill in the art can readily envision and produce further embodiments, based on the teachings herein, without undue experimentation.

All publications and patent applications mentioned in this Specification are herein incorporated by reference to the same extent as if each of them had been individually indicated to be incorporated by reference.

What is claimed is:

1. An isolated polynucleotide encoding an amino acid sequence consisting of SEQ ID NO: 3 or SEQ ID NO: 6.

2. An isolated polynucleotide selected from the group consisting of:
   a) SEQ ID NOS:1, 2, 4, or 5;
   b) SEQ ID NOS:1, 2, 4, or 5, wherein T can also be U;
   c) nucleotide sequences complementary to SEQ ID NOS:1, 2, 4, or 5; and
   d) fragments of a), b), or c) that are at least 15 bases in length that selectively hybridize to a), b), or c).

3. An expression vector containing a polynucleotide of claim 1.

4. The expression vector of claim 3, wherein the vector is a plasmid.

5. The expression vector of claim 3, wherein the vector is a viral vector.

6. A host cell transformed with an expression vector of claim 3.

7. The host cell of claim 6, wherein the cell is a eukaryotic cell.

8. The host cell of claim 6, wherein the cell is a prokaryotic cell.

9. An isolated polynucleotide comprising a nucleic acid molecule having a nucleotide sequence as set forth in
   a) SEQ ID NO:1, 2, 4, or 5; or
   b) SEQ ID NO:1, 2, 4, or 5 without a region coding for a signal peptide sequence.

10. The isolated polynucleotide of claim 9, further comprising a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 6,699,482 B2 | Page 1 of 1 |
| APPLICATION NO. | : 09/992807 | |
| DATED | : March 2, 2004 | |
| INVENTOR(S) | : Haake and Shang | |

It is certified that error appears in the above-identified patent and that said Letters Patent is hereby corrected as shown below:

Please delete the paragraph beginning on Line 9 of Column 1 and ending on Line 14 of Column 1 and replace with the following:

--This invention was made with Government support under Grant Nos. AI012601 and AI029733 awarded by the National Institutes of Health. The Government has certain rights in this invention.--

Signed and Sealed this

Second Day of June, 2009

JOHN DOLL
*Acting Director of the United States Patent and Trademark Office*